United States Patent [19]
Bouffard et al.

[11] Patent Number: 6,030,944
[45] Date of Patent: *Feb. 29, 2000

[54] CYCLOHEXAPEPTIDYL BISAMINE COMPOUNDS

[75] Inventors: Frances Aileen Bouffard, Scotch Plains; James F. Dropinski, Edison; Robert A. Zambias, Springfield, all of N.J.

[73] Assignee: Merck & Co., Inc., Rahway, N.J.

[ * ] Notice: This patent is subject to a terminal disclaimer.

[21] Appl. No.: 07/936,558

[22] Filed: Sep. 3, 1992

Related U.S. Application Data

[63] Continuation-in-part of application No. 07/771,027, Oct. 1, 1991, abandoned.

[51] Int. Cl.[7] .............................. A61K 38/12; C07K 7/54
[52] U.S. Cl. ................................. 514/11; 514/9; 514/2; 530/317; 530/318
[58] Field of Search .................... 514/11, 9, 2; 530/317, 530/318; 930/190, 200, 270, DIG. 546; 435/71.3, 71.1

[56] References Cited

U.S. PATENT DOCUMENTS

| | | | |
|---|---|---|---|
| 4,173,629 | 11/1979 | Dreyfuss et al. | 514/9 |
| 4,287,120 | 9/1981 | Abbott et al. | 530/317 |
| 4,293,485 | 10/1981 | Debono | 530/317 |
| 4,293,489 | 10/1981 | Debono | 530/317 |
| 4,320,054 | 3/1982 | Abbott et al. | 530/317 |
| 4,931,352 | 6/1990 | Fromtling et al. | 435/71.3 |
| 4,968,608 | 11/1990 | Giacobbe et al. | 435/71 |
| 5,021,341 | 6/1991 | Giacobbe et al. | 435/71.1 |
| 5,021,403 | 6/1991 | Sesin et al. | 514/9 |
| 5,166,135 | 11/1992 | Schmatz | 530/318 |

FOREIGN PATENT DOCUMENTS

| | | |
|---|---|---|
| 851310 | 8/1977 | Belgium . |
| 859067 | 3/1978 | Belgium . |
| 0 359 529 | 9/1989 | European Pat. Off. . |
| 0 405 997 | 6/1990 | European Pat. Off. . |
| 0 486 011A2 | 5/1992 | European Pat. Off. . |

OTHER PUBLICATIONS

U.S. application No. 07/963,332, Hammond et al., filed Oct. 19, 1992.
U.S. application No. 07/959,948, Zambias, filed Oct. 15, 1992.
U.S. application No. 07/960,983, Bouffard et al., filed Oct. 16, 1992.
U.S. application No. 07/775,773, Bouffard et al., filed Oct. 17, 1991.
The Merck Manual of Diagnosis & Therapy, p. 881, (1966).

*Primary Examiner*—Ponnathapura Achutamurthy
*Assistant Examiner*—T. D. Wessendorf
*Attorney, Agent, or Firm*—Elliott Korsen; Mark R. Daniel

[57] ABSTRACT

Certain bisamine compounds which have a cyclohexapeptidyl nucleus and which are found to have antibiotic activity with physical properties suitable for direct use in therapeutic compositions are described. A novel process for their preparation is also described.

14 Claims, No Drawings

CYCLOHEXAPEPTIDYL BISAMINE COMPOUNDS

This application is a continuation-in-part of application Ser. No. 07/771,027, filed Oct. 1, 1991 abandoned.

The present invention is directed to certain cyclohexapeptidyl bisamine compounds and to a process for their preparation.

The cyclohexapeptidyl bisamine compounds of the present invention, Compound X (SEQ ID NOS 1–7) have one amine group directly on the ring and the second amine group as a substituent on the ether group, and may be represented as (A) an amine, Compound X-I (SEQ ID NOS 1–7, 29), represented by the formula:

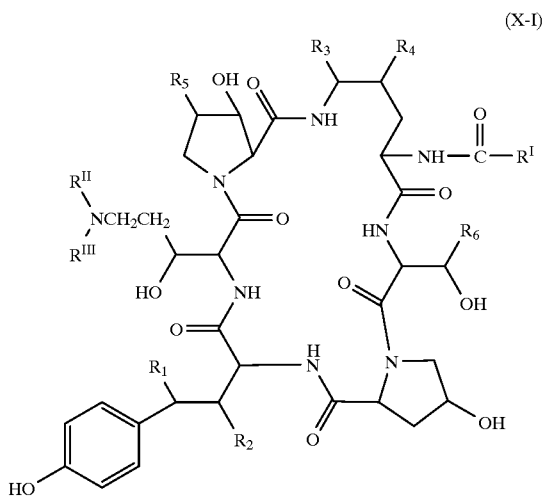

(X-I)

or its acid addition salt, or (B) a quaternary ammonium salt, Compound X-II (SEQ ID NOS 1–7, 29), represented by the formula

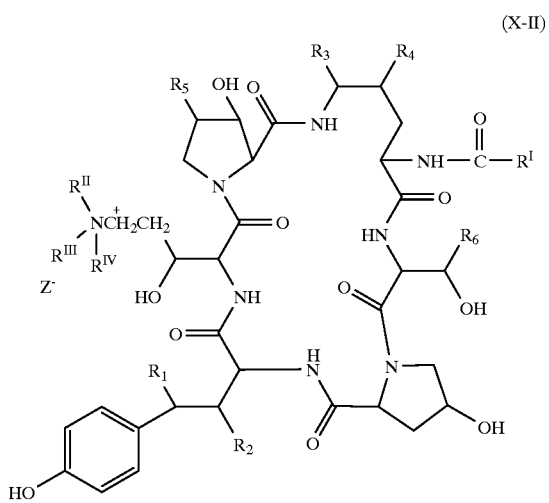

(X-II)

In the foregoing and succeeding formulas, $R_1$ is H or OH $R_2$ is H or OH $R_3$ is $QC_nH_{2n}NR^VR^{VI}$, $QC_nH_{2n}NR^VR^{VI}R^{VII+}Y^-$, or $Q(CH_2)_{1-3}CR^{VIII}R^{IX}NHR^X$ $R_4$ is H or OH $R_5$ is H, OH or $CH_3$ $R_6$ is H or $CH_3$ $R^I$ is $C_9$–$C_{21}$ alkyl, $C_9$–$C_{21}$ alkenyl, or $C_1$–$C_{10}$ alkoxyphenyl, or $C_1$–$C_{10}$ alkoxynaphthyl $R^{II}$ is H, $C_1$–$C_4$ alkyl or benzyl, $R^{III}$ is H, $C_1$–$C_4$ alkyl or benzyl or $R^{II}$ and $R^{III}$ together is —$(CH_2)_4$— or —$(CH_2)_5$—

$R^{IV}$ is H or $C_1$–$C_4$ alkyl;

$R^V$ is H, $C_1$–$C_4$ alkyl or benzyl $R^{VI}$ is H, $C_1$–$C_4$ alkyl or benzyl or $R^V$ and $R^{VI}$ together is —$(CH_2)_4$— or —$(CH_2)_5$—

$R^{VII}$ is H or $C_1$–$C_4$ alkyl $R^{VIII}$ is H, $(CH_2)_mH$, $(CH_2)_mOH$, $(CH_2)_mNH_2$ or COX wherein X is $NH_2$, OH or $O(CH_2)_mH$ $R^{IX}$ is H, $(CH_2)_mH$, or together with $R^{VIII}$ is =O(carbonyl);

$R^X$ is H (except when $R^{VIII}$ and $R^{IX}$ are H), C(=NH)NH_2, C(=NH)(CH_2)_{0-3}H, CO(CH_2)_{0-3}H, CO(CH_2)_mNH_2, (CH_2)_{2-4}OH or (CH_2)_{2-4}NH_2.

Q is O or S

Y is an anion of a pharmaceutically acceptable salt z is an anion of a pharmaceutically acceptable salt each m is independently an integer from 1 to 3, inclusive, and n is an integer from 2 to 4, inclusive.

Hereinafter, when the expression "bisamine compound" or "Compound X" is employed, it is intended to embrace the amine of formula (X-I), its acid addition salt or salts and quaternary ammonium salt of formula (X-II). "Compound X-I" will refer to the acid addition salt as well as the free base. It is to be noted that in both Compounds X-I and X-II, $R_3$ may be either an amino alkyl ether or a quaternary ammonium alkyl ether. Thus, the bisamine compound may be an uncharged compound having two amino groups or it may be a mono ammonium or a bis ammonium compound. Thus, when the "bisamine compound" is an amine, as above defined (Compound X-I) and $R_3$ is $QC_nH_{2n}NR^VR^{VI}$ or $Q(CH_2)_{1-3}CR^{VIII}R^{IX}NHR^X$, the ultimate compound is uncharged and may be referred to generically as Compound X-Ia, Compound X-Ia may be represented by the following formula:

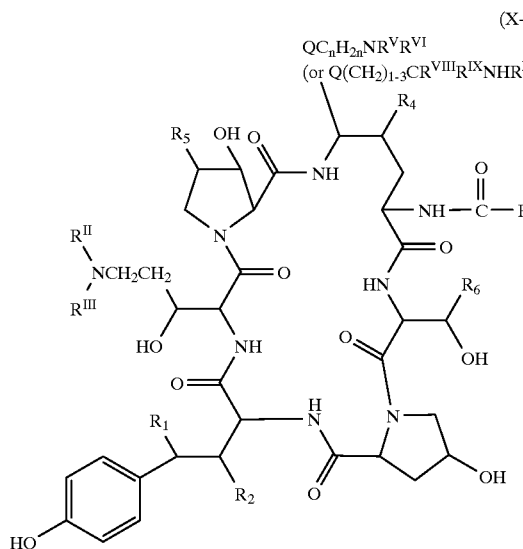

(X-Ia)

When the "amine compound" is an amine (Compound X-I) and $R_3$ is $QC_nH_{2n}NR^VR^{VI}R^{VII+}Y^-$, the charged portion of the molecule will reside in the amino ether portion and the compound may be referred to as Compound X-Ib. Compound X-Ib may be represented by the following formula:

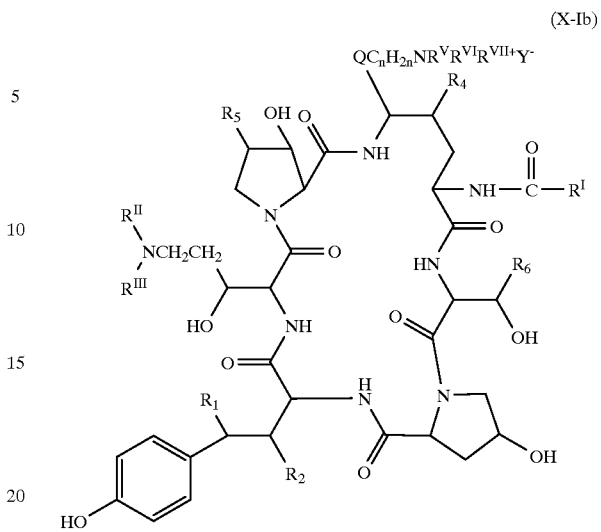

(X-Ib)

When the "amine compound" is a quaternary ammonium salt (Compound X-II) and $R_3$ is $QC_nH_{2n}NR^VR^{VI}$ or $Q(CH_2)_{1-3}CR^{VIII}R^{IX}NHR^X$ the ultimate compound will be a monoquaternary ammonium salt and the compound may be referred to as Compound X-IIa. Compound X-IIa may be represented by the following formula:

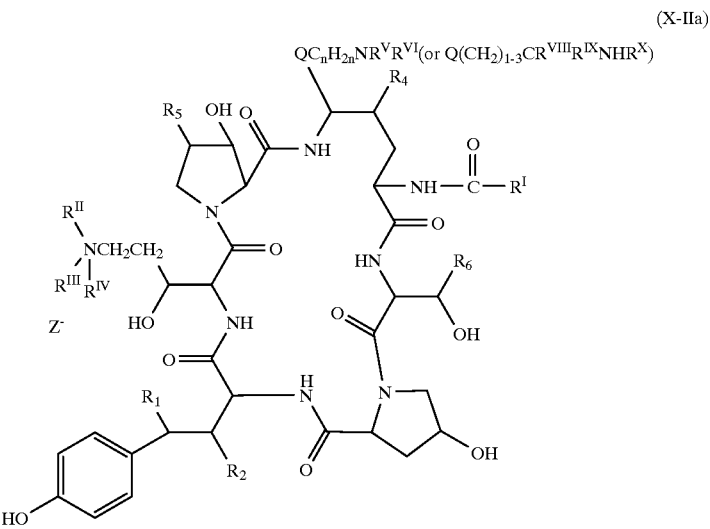

(X-IIa)

When the "amine compound" is a quaternary ammonium salt (Compound X-II) and $R_3$ is $-QC_nH_{2n}NR^VR^{VI}R^{VII+}Y^-$, the resulting compound will be a bis-quaternary salt and may be referred to as Compound X-IIb. Compound X-IIb may be represented by the following formula:

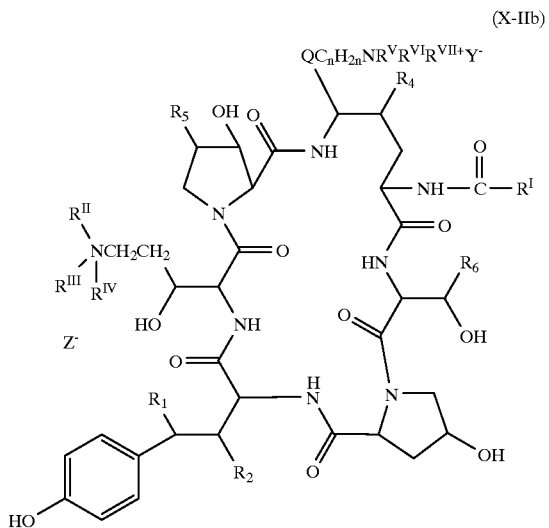

(X-IIb)

Where the expression "alkyl", "alkenyll" or "alkoxy" is employed, it is intended to include branched as well as straight chain radicals.

Where the expression "ether" is employed, it is intended to include thioethers as will be evident from the context.

Pharmaceutically acceptable salts suitable as acid addition salts as well as salts providing the anion of the quaternary salt are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in Journal of Pharmaceutical Science, 66, 2 (1977).

Representative nuclei for the bisamine compounds, Compound X, and the sequence ID for these compounds may be seen in the following table. Since the peptide nuclei would be the same irrespective of substituents $R^I$, $R^{II}$, $R^{III}$, or $R^{IV}$ and since the sequence identification number is assigned for the nuclear variations, the amines and ammonium salts have the same sequence ID's. Also, since the nucleus amino acid would be the same irrespective of the particular amino alkyl ether, i.e., irrespective of $R^V$, $R^{VI}$ or $R^{VII}$, $R_3$ is considered to be the same for purposes of sequence identification and is not on the table. Further, since the amino acid is not varied irrespective of the change in the lipophilic side chain, separate sequence numbers are not assigned merely on the basis of a different side chain. "Lipophilic side chain" as herein employed refers to $R^I$.

| BISAMINE COMPOUND NUCLEI | $R_1$ | $R_2$ | $R_4$ | $R_5$ | $R_6$ | SEQ. ID |
|---|---|---|---|---|---|---|
| X-1 | OH | OH | OH | H | CH$_3$ | 1 |
| X-2 | OH | OH | OH | CH$_3$ | CH$_3$ | 2 |
| X-3 | H | OH | OH | CH$_3$ | H | 3 |
| X-4 | OH | H | OH | CH$_3$ | CH$_3$ | 4 |
| X-5 | H | H | H | CH$_3$ | CH$_3$ | 5 |
| X-6 | OH | OH | OH | OH | CH$_3$ | 6 |
| X-7 | H | OH | OH | H | H | 7 |
| X-8 | H | OH | OH | H | CH$_3$ | 29 |

A compound which is particularly outstanding for the control of mycotic infections is Compound X-Ia-1 (Seq. ID No. 1) represented by the following formula:

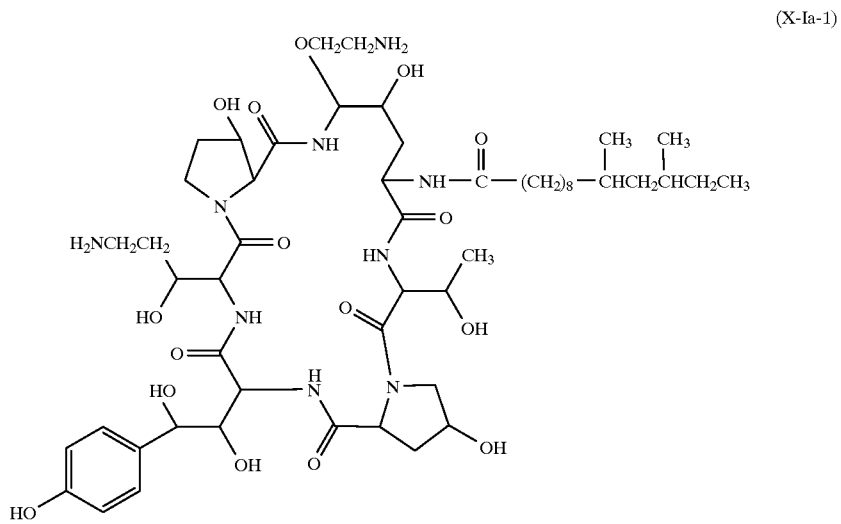

(X-Ia-1)

When the compounds are free amines, they are soluble in lower alcohols and polar aprotic solvents such as dimethylformamide (DMF) and pyridine. They are insoluble in solvents such as ether and acetonitrile. When the compounds are quaternary ammonium salts or protonated amines, they are soluble in water and polar solvents.

The compounds of the present invention are useful as an antibiotic, especially as an antifungal agent or as an antiprotozoal agent. As antifungal agents they are useful for the control of both filamentous fungi and yeasts. They are especially adaptable to be employed for the treatment of mycotic infections in mammals, especially those caused by Candida species such as *C. albicans, C. tropicalis* and *C. pseudotropicalis*, and Aspergillus species such as *A. fumigatus, A. flavus* and *A. niger*. They are also useful for the treatment and/or prevention of *Pneumocystis carinii* pneumonia to which immune compromised patients are especially susceptible as hereinafter described.

The previously noted solubility properties are advantageous for utilization in therapeutic applications, especially in injectible compositions.

The compounds of the present invention may be obtained from natural products or derivatives of natural products through a sequence of reactions seen in the accompanying flow diagram or from one of the intermediates which are claimed in concurrently filed copending applications.

The starting material represented by formula (E), which is generally a natural product but also may be a side chain derivative of a natural product and which may be obtained as hereinafter described, is first subjected to dehydration (Step A) to produce a nitrile of formula (F) which is then reduced (Step B) to an amine, which if a substituted amine is desired, may be alkylated by reductive alkylation with an appropriate aldehyde and a reducing agent such as sodium cyanoborohydride to obtain Compound G.

When Compound G has a nuclear configuration which is different from that obtained from a natural product, it may be obtained by reduction of an OH.

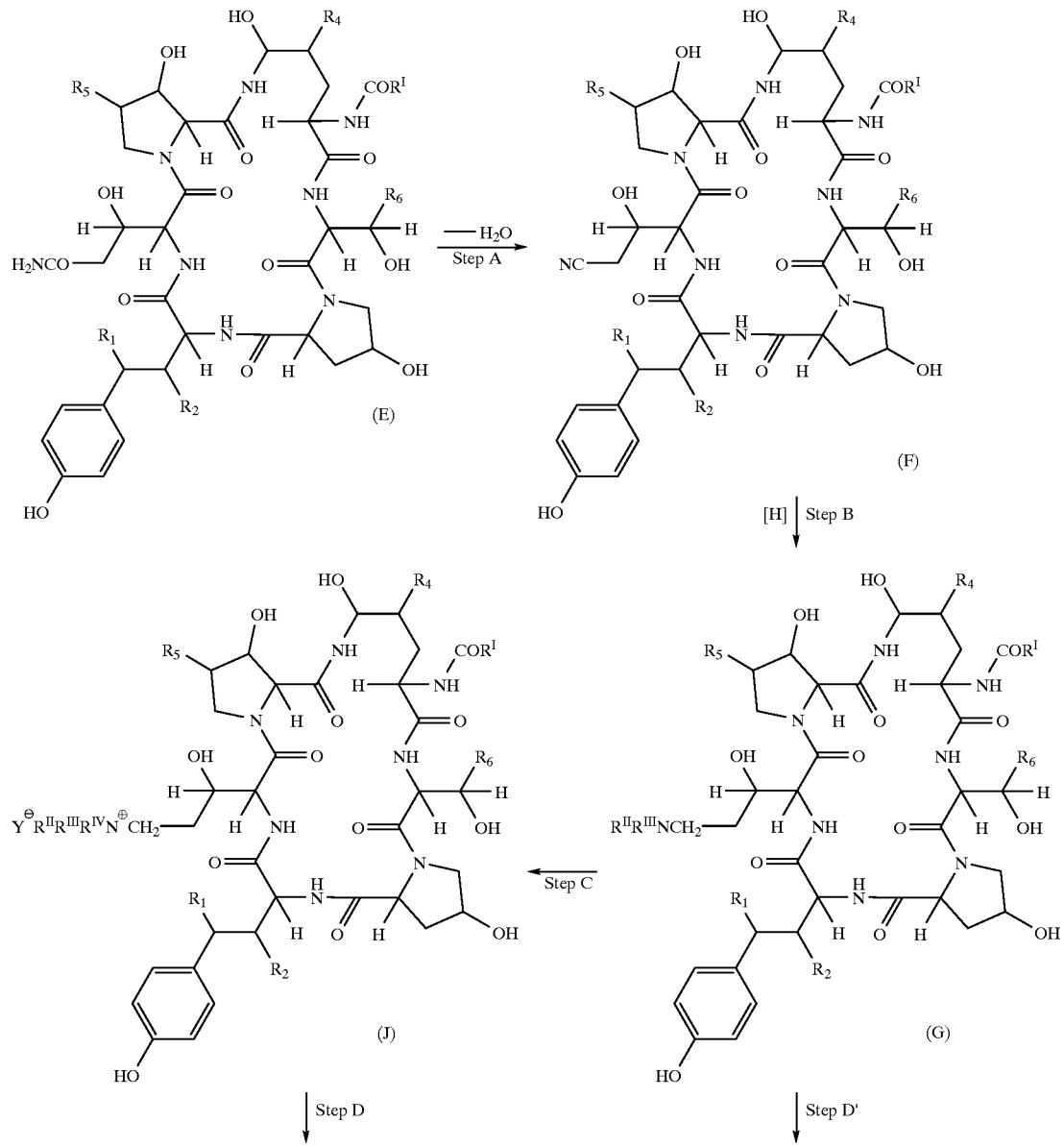

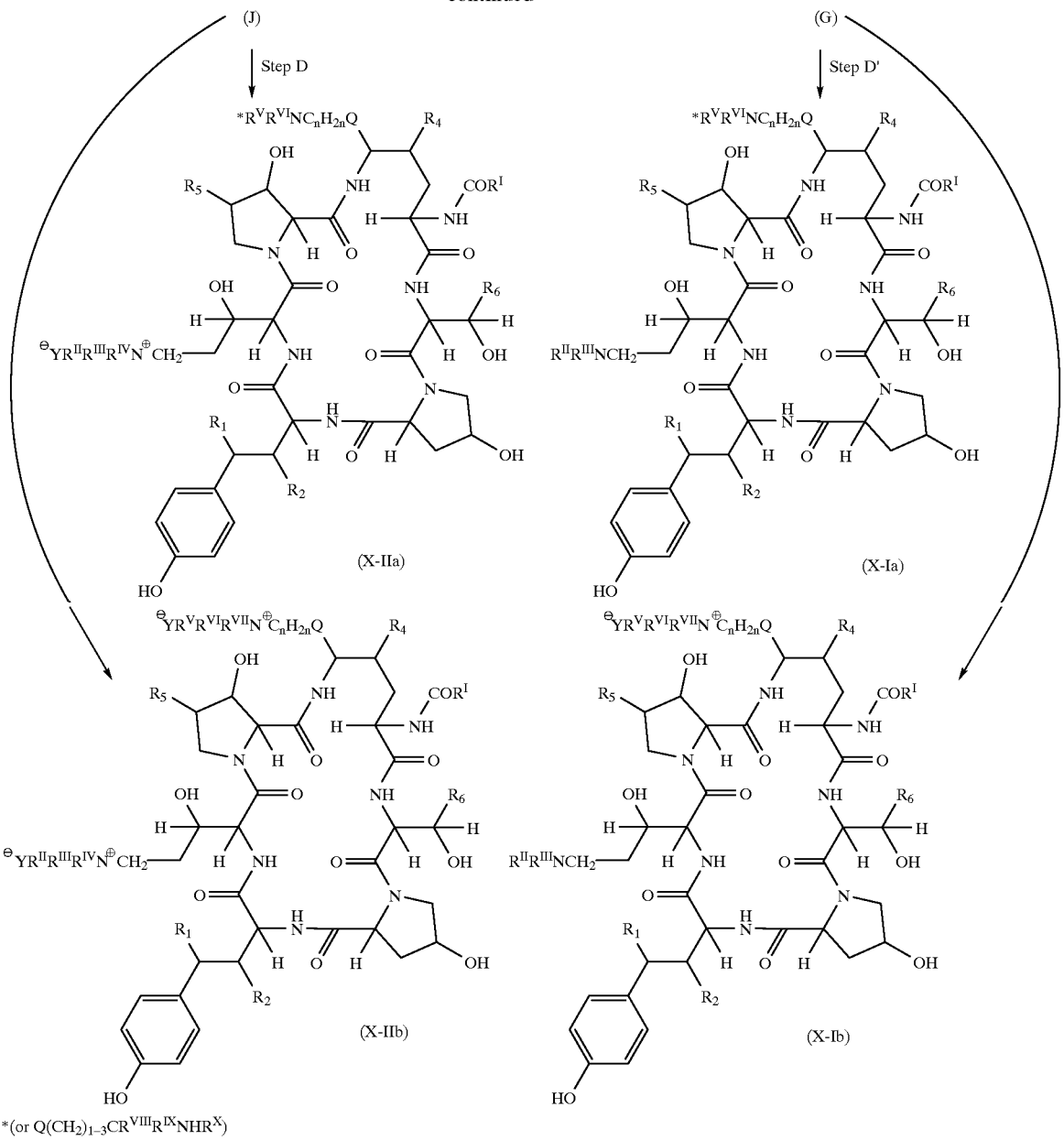

The amine may be quaternized to Compound J, by causing the amine to react with an excess alkylating agent such as alkyl halide or alkyl sulfate in the presence of a mild base such as sodium bicarbonate in an inert solvent (Step C.) When all the substituents on the nitrogen are the same, the starting amine may be the primary amine (Compound G, $R^{II}$ and $R^{III}$ are H).

Compounds F, G, and J are novel compounds which are claimed in concurrently filed copending application Ser. Nos. 07/936,434 and 07/936,561; which are continuation-in-part applications of concurrently filed applications Ser. No. 07/771,018 abandoned (Attorney Docket No. 18531) and Ser. No. 07/771,017 abandoned (Attorney Docket No. 18530).

Compound G or J may be converted to the aminoalkyl ether by adding 1 to 10 equivalents of strong organic or mineral acid such as camphorsulfonic acid or hydrochloric acid to a solution of cyclohexapeptidyl propanolamine (Compound G) or the cyclohexapeptidyl propanolammonium compound (Compound J) and 20 to 200 equivalents of the appropriate amino alcohol or aminothiol in the form of an acid addition salt, such as the hydrochloride or hydrobromide, in an appropriate solvent such as dimethyl-sulfoxide (DMSO) or dimethylformamide (DMF) and the mixture stirred at room temperature for one to seven days. The reaction is monitored by HPLC and when determined to be complete, the reaction mixture is diluted with 5 to 50 volumes of water and the entire mixture applied to reverse phase chromatography column. "LICHROPREP" C-18 (E. Merck) column is representative of an appropriate column. The column is then eluted with a weakly eluting solvent such as 5 percent acetonitrile in water (containing 0.1 percent trifluoroacetic (TFA) acid or acetic acid) to remove excess amino-alcohol or aminothiol, then with a stronger eluting solvent such as 10 to 50 percent acetonitrile to elute the product. Fractions containing the desired amine compound may be combined and concentrated to isolate the acid addition salt, Compound X-IIa or X-Ia, according to Steps D or D' respectively.

Compound G or J may be converted to Compound X-IIb or Compound X-Ib in a similar manner by adding 1–10 equivalents of a strong organic or mineral acid to a stirred solution of cyclohexapeptidyl propanolamine or cyclohexapeptidyl propanolammonium salt and 20 to 200 equivalents of the appropriate alkylammonium alcohol or thiol in an appropriate solvent such as DMSO or DMF, and the mixture stirred at room temperature for one to seven days until substantial completion of the reaction as can be determined by HPLC. The reaction mixture is then diluted with 5 to 50 volumes of water and the entire mixture applied to a reverse phase chromatography column. The column then may be eluted with a weakly eluting solvent such as 5 percent acetonitrile to remove excess amino alcohol or thiol and then with 10 to 50 percent acetonitrile to elute the product X-Ib or X-IIb.

As can be seen from the foregoing flow diagram, the amino acids in the nucleus remain the same except at the hydroxyglutamine. The aminoalkyl ethers giving rise to compounds which may be identified as bis amines are derivatives which do not change the nature of the amino acids. The sequence identification of the amines or ammonium compounds (at the original hydroxyglutamine) from which the aminoalkyl ethers or thioethers are made would be the same since the amine and hydroxy group of the amino acid remain unchanged. The sequence identification of the starting material and nitrile intermediate are given below.

The sequence identification of the starting materials for the dehydration step are:

| STARTING MATERIAL (E) | $R_1$ | $R_2$ | $R_4$ | $R_5$ | $R_6$ | SEQ. ID |
|---|---|---|---|---|---|---|
| E-1 | OH | OH | OH | H | $CH_3$ | 8 |
| E-2 | OH | OH | OH | $CH_3$ | $CH_3$ | 9 |
| E-3 | H | OH | OH | $CH_3$ | H | 10 |
| E-4 | OH | H | OH | $CH_3$ | $CH_3$ | 11 |
| E-5 | H | H | H | $CH_3$ | $CH_3$ | 12 |
| E-6 | OH | OH | OH | OH | $CH_3$ | 13 |
| E-7 | H | OH | OH | H | H | 14 |

The sequence identification of the nitriles are:

| NITRILE COMPOUND (F) | $R_1$ | $R_2$ | $R_4$ | $R_5$ | $R_6$ | SEQ. ID |
|---|---|---|---|---|---|---|
| F-1 | OH | OH | OH | H | $CH_3$ | 15 |
| F-2 | OH | OH | OH | $CH_3$ | $CH_3$ | 16 |
| F-3 | H | OH | OH | $CH_3$ | H | 17 |
| F-4 | OH | H | OH | $CH_3$ | $CH_3$ | 18 |
| F-5 | H | H | H | $CH_3$ | $CH_3$ | 19 |
| F-6 | OH | OH | OH | OH | $CH_3$ | 20 |
| F-7 | H | OH | OH | H | H | 21 |

The sequence identification of the propanolamines or the quaternary salts are:

| PROPANOLAMINE/ PROPANO-LAMMONIUM COMPOUND | $R_1$ | $R_2$ | $R_4$ | $R_5$ | $R_6$ | SEQ. ID |
|---|---|---|---|---|---|---|
| G/J-1 | OH | OH | OH | H | $CH_3$ | 22 |
| G/J-2 | OH | OH | OH | $CH_3$ | $CH_3$ | 23 |
| G/J-3 | H | OH | OH | $CH_3$ | H | 24 |
| G/J-4 | OH | H | OH | $CH_3$ | $CH_3$ | 25 |
| G/J-5 | H | H | H | $CH_3$ | $CH_3$ | 26 |
| G/J-6 | OH | OH | OH | OH | $CH_3$ | 27 |
| G/J-7 | H | OH | OH | H | H | 28 |

The first step in the preparation of Compound X-I (Seq. ID Nos. 1–7) is the dehydration of the carboxamide group of Compound E to the nitrile of Compound F. The reaction is preferably carried out under nitrogen with cyanuric chloride in a solvent in the presence or absence of molecular sieves.

Suitable reagents which may be employed in place of cyanuric chloride are anhydrides such as acetic anhydride, trifluoroacetic anhydride and phosphorus pentoxide; acid chlorides such as oxalyl chloride, phosphorus oxychloride, thionyl chloride, p-toluenesulfonyl chloride and chlorosulfonyl isocyanate; phosphonium reagents such as phosphorus pentachloride, triphenylphosphine/carbon tetrachloride, triphenylphosphonium ditriflate and triphenylphosphonium dichloride; carbodiimides such as dicyclohexylcarbodiimide; other dehydrating agents such as aluminum chloride, titanium tetrachloride, ethyl(carboxysulfamoyl) triethylammonium hydroxide inner salt.

Suitable solvents include dimethylformamide or weakly basic solvents such as pyridine, collidine and the like.

Molecular sieves may be in the size range 3A to 5A.

The relative amounts of Compound E (Seq. ID Nos. 8–14) and reagents vary, but in general the dehydrating agent is used in excess. From about 1.5 to 15 equivalents of the dehydrating agent are employed. When employed the molecular sieves are used in amounts of at least tenfold by weight.

In carrying out the reaction, a suspension of molecular sieves in a rigorously dried solvent is first prepared, and while stirring under an atmosphere of nitrogen, there is added, cyanuric chloride or other dehydrating agent and thoroughly mixed. To the resulting mixture while stirring under an atmosphere of nitrogen is added the starting material, Compound E and the stirring continued for about 12 to 24 hours or until HPLC analysis of the reaction mixture indicates substantial completion of the reaction with the formation of the nitrile. When the HPLC analysis shows substantial completion of the reaction, the sieves are removed by filtration, preferably on a sintered glass funnel, and the filtrate concentrated and purified by preparative HPLC. The mobile phase used in the purification are varying ratios of a water/acetonitrile composition and an acetonitrile/water composition. These compositions are referred to in the examples as A and B. Composition A is 95/5 water/acetonitrile containing 0.1% trifluoroacetic acid (TFA) or acetic acid. Composition B is 95/5 acetonitrile/water containing 0.1% TFA or acetic acid. The exact mobile phase used for HPLC assays and the mobile phase used in preparative HPLCs may differ not only from each other but also from compound to compound, but can be determined by the skilled artisan without difficulty.

In carrying out the reaction in the absence of sieves, solid cyanuric chloride is added in a single portion to a solution of Compound E in an aprotic solvent and stirred rapidly for a short time and the reaction mixture then quenched by adding aqueous sodium acetate directly to the reaction mixture. The volatiles are then removed in vacuo to obtain a solid residue which may be purified as above described.

The reduction of the nitrile to the amine may be carried out employing either chemical or catalytic reduction. Sodium borohydride with cobaltous chloride in alcoholic solvent has been found to be particularly useful. When this combination of reagents is used, from about 5 to 50 molar equivalent of sodium borohydride and from 2 to 10 molar equivalents of cobaltous chloride are used for each molar amount of the nitrile.

Other hydride reducing agents such as sodium cyanoborohydride, aluminum hydride, diborane, diisobutyl aluminum hydride and the like also may be used. Frequently these reducing agents are used in combination with a Lewis acid such as cobaltous chloride or aluminum chloride as in the present combination of sodium borohydride and cobaltous chloride.

Catalytic hydrogenation also may be carried out over a variety of catalysts including palladium on carbon, platinum oxide, or rhodium on alumina.

Typical solvents depending on the reagent include alcohols, especially methanol and ethanol, dimethylformamide, pyridine, tetrahydrofuran or other ethers.

When the reduction of the nitrile to the amine is carried out using the preferred chemical procedure, the reaction may be carried out by adding the chemical reducing agent to the nitrile in an alcoholic solution under an atmosphere of nitrogen, and stirring until HPLC analysis using detection by ultraviolet absorption at 210 nm shows substantial completion of the reaction. When sodium borohydride is used in combination with cobaltous chloride, cobaltous chloride is added while stirring to a solution in methanol, or other solvent, of the nitrile, prepared as above described, at ambient temperature, followed by portionwise addition of the sodium borohydride which is accompanied by gas evolution. Stirring is continued for from 12 to 24 hours. The mixture may be quenched with acetic or hydrochloric at this time. Then the mixture is diluted with a highly aqueous mobile phase, 70/30 to 50/50 A:B, may be acidified with acetic acid or hydrochloric acid, filtered and purified by chromatography. The eluate fractions are lyophilized to obtain the amine as an acetic acid, trifluoroacetic acid or hydrochloric acid addition salt.

The N-alkylated or benzylated compounds may be prepared using any suitable known procedure for preparing secondary or tertiary amines. The N-benzyl compound is best prepared by first preparing a Schiff base with benzaldehyde and thereafter reducing with conventional reducing agents such as those previously noted in connection with the reduction of the nitrile although milder reducing agents may be employed.

When the desired alkyl group on the nitrogen is methyl, the carbon may be introduced by formylating, followed by reduction of the hydroxymethyl group with sodium cyanoborohydride or other reducing agent. When the desired alkyl group on the nitrogen is a higher alkyl, a preferred procedure is a reductive alkylation of an N-benzyl derivative with an aldehyde and a reducing agent such as sodium cyanoborohydride, and purifying the product with reverse phase chromatography to obtain a benzyl and a higher alkyl substituted tertiary amine. The benzyl group may be removed by hydrogenation using palladium on carbon or other suitable catalyst.

When the alkyl groups are the same, the same general procedure is preferably employed. Although alkyl halide or sulfate may be employed, these are best for quaternary salts.

When a quaternary ammonium salt is to be prepared, the appropriate amine prepared as above described is caused to react with an alkylating agent such as alkyl iodide, other alkyl halide, or alkyl sulfate in the presence of sodium bicarbonate in an inert solvent. A slight molar excess of sodium bicarbonate is employed. The alkylating agent is used in large molar excess. About six to tenfold molar excess may be employed.

When all substituents on the nitrogen are the same, the starting amine may be the primary amine. For mixed amines, it is preferable to enter the specific groups first since alkylation using an alkylating agent is more difficult to control.

To prepare the aminoalkyl ethers camphorsulfonic acid is added to the solution containing cyclohexapeptidyl propanolamine compound (Compound G), the appropriate aminoalkanol or aminoalkylthiol hydrochloride salt or N-carbobenzyloxy (CBZ) protected aminoalkanol or aminoalkylthiol and camphorsulfonic acid or hydrogen chloride are mixed together and the mixture allowed to stir at room temperature for one to seven days. The progress of the reaction is conveniently monitored by HPLC using acetonitrile/water as the eluting agent. After the reaction is substantially complete, the reaction mixture is diluted with water and the resulting solution applied to a reverse phase flash silica gel column and eluted with an appropriate mixture of acetonitrile and water to obtain the desired bisamine compound, or the CBZ protected bisamine compound. In the case of the latter, the protective CBZ group is removed by hydrogenolysis.

Although other alkylating agents such as substituted or protected aminoalkyl halides or sulfates (for substituted or free aminoalkyl ethers) may be employed the salt of the free base in the presence of camphorsulfonic acid or hydrogen chloride has been found to be most effective and convenient.

A large excess of the aminoalkanol or aminoalkylthiol is employed, preferably of the order of one-hundred molar equivalents. The amount of camphorsulfonic acid or hydrogen chloride is about two moles for every mole of the cyclohexapeptidyl propanolamine. The reaction medium is a suitable aprotic solvent such as dimethylsulfoxide (DMSO) or dimethylformamide (DMF) or dioxane, or combinations thereof.

For monitoring the progress of the reaction, an analytical "ZORBAX" (DuPont) column with 10 to 50 percent aqueous acetonitrile containing 0.1 percent trifluoroacetic acid (TFA) or acetic acid is suitable. For preparative purification, a reverse phase column such as "LICHROPREP" C18 of particle size 40–63 microns with 5–15 percent aqueous acetonitrile to remove solvent and 10 to 50 percent acetonitrile (containing 0.1% TFA or acetic acid) to elute the product is useful.

When it is desired that both the propanolamine portion of the molecule and the aminoether or aminothioether portion of the molecule be in the quaternary ammonium form, conventional alkylating agents may be employed either on the unsubstituted amino ether or thioether or on a substituted ammonium ether or thioether. When the ether is an unsubstituted amino ether, generally, the alkylammonium group will be a trialkylammonium group in which all alkyls will be the same. If mixed substitution is desired on the amino group, alkylation of a substituted aminoalkyl ether is carried out to obtain the quaterary ammonium ether compound.

The compounds of the present invention are active against many fungi and particularly against Candida, Aspergillus and Cryptococcus species. The antifungal properties may be illustrated with the minimum fungicidal concentration (MFC) determination against certain Candida and Cryptococcus organisms in a microbroth dilution assay carried out in a Yeast Nitrogen Base (Difco) medium with 1 percent dextrose (YNBD).

In a representative assay, Compound X-Ia-1 was solubilized in 100 percent dimethyl sulfoxide (DMSO) at an initial concentration of 5 mg/ml. Once dissolved, the drug stock was brought to a concentration of 512 µg/ml by dilution in water such that the final DMSO concentration was about 10 percent. The solution was then dispensed via a multichannel pipetter into the first column of a 96-well plate (each well containing 0.075 ml of YNBD), resulting in a drug concentration of 256 µg/ml. Compounds in the first column were diluted 2-fold across the rows yielding final drug concentrations ranging from 256 µg/ml to 0.12 µg/ml.

Four-hour broth cultures of organisms to be tested were adjusted using a spectrophotometer at 600 nm to equal a 0.5 McFarland Standard. This suspension was diluted 1:100 in YNBD to yield a cell concentration of $1$–$5 \times 10^4$ colony forming units (CFU)/ml. Aliquots of the suspension (0.075 ml) were inoculated into each well of the microtiter plate resulting in a final cell inoculum of $5$–$25 \times 10^3$. CFU/ml and final drug concentrations ranging from 128 µg/ml to 0.06 µg/ml. Each assay includes one row for drug-free control wells and one row for cell-free control wells.

After 24 hours of incubation, the microtiter plates were shaken gently on a shaker to resuspend the cells. The MIC-2000 inoculator was used to transfer a 1.5 microliter sample from each well of the 96-well microtiter plate to a single reservoir inoculum plate containing Sabouraud dextrose agar (SDA). The inoculated SDA plates were incubated for 24 hours at 35° C. However, for *Cryptoccoccus neoformans* strains, SDA plates were inoculated at 48 hours and incubated 48 hours after being spotted on SDA before making minimum fungicidal concentration (MFC) readings. The results were as follows:

| Organism | | MFC µg/mL |
|---|---|---|
| C. albicans | MY 1028 | <0.06 |
| C. albicans | MY 1055 | 0.12 |
| C. albicans | MY 1750 | 0.12 |
| C. guillermondii | MY 1019 | 0.5 |
| C. parapsilosis | MY 1010 | 0.12 |
| C. pseudotropicalis | MY 1100 | 0.12 |
| C. tropicalis | MY 1012 | <0.06 |
| Cr. neoformans | MY 1051 | 16 |
| Cr. neoformans | MY 1146 | 16 |
| Cr. neoformans | MY 2061 | 16 |
| Cr. neoformans | MY 2062 | 16 |

The compounds also show in vivo effectiveness against fungi which may be demonstrated with Compound X-Ia-1.

Growth from an overnight SDA culture of *Candida albicans* MY 1055 was suspended in sterile saline and the cell concentration determined by hemacytometer count and the cell suspension adjusted to $3.75 \times 10^5$ cells/ml. Then 0.2 milliliter of this suspension was administered I.V. in the tail vein of mice so that the final inoculum was $7.5 \times 10^4$ cells/mouse.

The assay then was carried out by administering aqueous solutions of Compound X-Ia-1 at various concentrations intraperitoneally (I.P.), twice daily (b.i.d.) for four consecutive days to 18 to 20 gram female DBA/2 mice, which previously had been infected with *Candida albicans* in the manner described above. Distilled water was administered I.P. to *C. albicans* challenged mice as controls. After seven days, the mice were sacrificed by carbon dioxide gas, paired kidneys were removed aseptically and placed in sterile polyethylene bags containing 5 milliters of sterile saline. The kidneys were homogenized in the bags, serially diluted in sterile saline and aliquots spread on the surface of SDA plates. The plates were incubated at 35° C. for 48 hours and yeast colonies were enumerated for determination of colony forming units (CFU) per gram of kidneys. Compound X-Ia-1 showed greater than 99 percent reduction of recoverable Candida CFUs at 1.5 and 0.38 mg/kg I.P. twice daily for seven consecutive days.

The compounds of the present invention may also be useful for inhibiting or alleviating *Pneumocystis carinii* infections in immune compromised patients. The efficacy of the compounds of the present invention for therapeutic or anti-infective purposes may be demonstrated in studies on immunosuppressed rats.

In a representative study, the effectiveness of Compound X-Ia-1 was determined. Sprague-Dawley rats (weighing approximately 250 grams) were immunosuppressed with dexamethasone in the drinking water (2.0 mg/L) and maintained on a low protein diet for seven seeks to induce the development of pneumocystis pneumonia from a latent infection. Before drug treatment, two rats were sacrificed to confirm the presence of *Pneumocystis carinii* pneumonia (PCP); both rats were found to have infections. Five rats (weighing approximately 150 grams) were injected twice daily for four days subcutaneously (sc) with Compound X-Ia$^{-1}$ in 0.25 ml of vehicle (distilled water). A vehicle control was also carried out. All animals continued to receive dexamethasone in the drinking water and low protein diet during the treatment period. At the completion of the treatment, all animals were sacrificed, the lungs were removed and processed, and the extent of disease determined by microscopic analysis of stained slides. The results of this study showed Compound X-Ia$^{-1}$ was 90 percent effective in reducing *P. carinii* cysts in 5 rats when dosed at 0.019 mg/kg.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1 percent by weight of Compound X or one of the components. Concentrate compositions suitable for dilutions prior to use may contain 90 percent or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound X with the components suitable for the medium desired.

Compositions formulated for oral administration may be a liquid composition or a solid composition. For liquid preparations, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with a lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and for injecton take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound also may be solubilized in alcohol/propylene glycol or polyethylene glycol for drip intravenous administration. These compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is for antifungal use any method of administration may be employed.

When the compound is to be employed for control of pneumocystis infections any method may be employed although it may be desirable to directly treat lung and bronchi. In such administration inhalation methods are employed. For administration by inhalation, the compounds of the present invention are conveniently delivered in the form of an aerosol spray presentation from pressurized packs or nebulisers. The preferred delivery system for inhalation is a metered dose inhalation (MDI) aerosol, which may be formulated as a suspension or solution of Compound X-I or X-II in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

EXAMPLE I

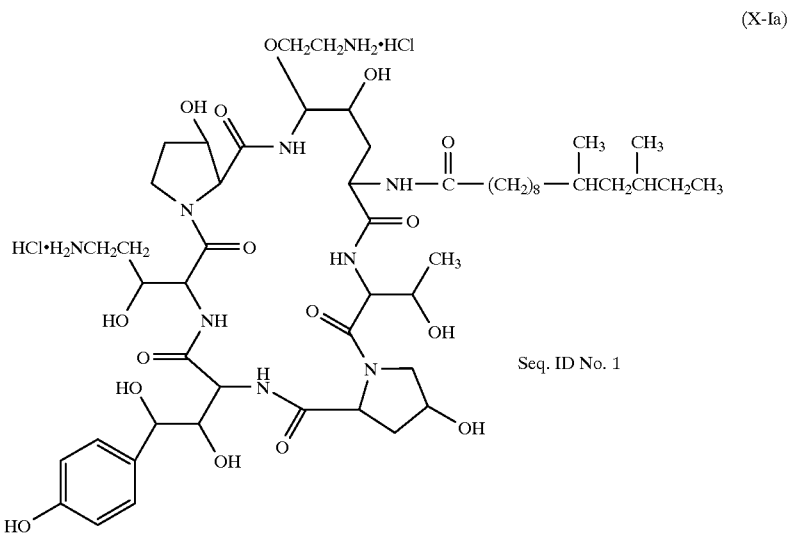

(X-Ia)

Seq. ID No. 1

A. Preparation of Intermediate Nitrile Compound (Compound F-Ia) (Seq ID No. 15)

1.38 grams (7.48 mmol; 1.5 molar eq) of cyanuric chloride was added to a suspension of 4A molecular sieves pre-prepared by stirring together under nitrogen for 0.5 hour 25.5 grams of 4 Å molecular sieves in 115 milliliters of DMF (predried over a combination of 13X and 3 Å molecular sieves), and the stirring continued for 5 minutes. To the resulting suspension was added 5.2 grams (4.9 mmol) of Compound E-1 (Seq. ID No. 8) ($R_1$, $R_2$, $R_3$ and $R_4$ are OH; $R_5$ is H; $R_6$ is $CH_3$; $R^I$ is 9,11-dimethyltridecyl). The resulting mixture was then stirred for 22 hours. At the end of this period an HPLC analysis was carried out employing a "ZORBAX" (4.9 mm×25 cm) C8 column and eluting isocratically with 45/55 water:acetonitrile (A:B) (containing 0.1% TFA) at ambient temperature with detection by ultraviolet absorption at 210 nm which showed a preponderance of product. The molecular sieves were filtered onto a sintered glass funnel and washed consecutively with 15 milliliters of DMF and 20 milliliters of methanol. The filtrate was concentrated in vacuo to a thick oil. The oil was absorbed in 20 milliliters of 60/40 A:B mobile phase and 10 milliliters of methanol and filtered through a 0.45μ Whatman polypropylene syringe filter. The filtrate was washed with mobile phase 60/40 A:B to a volume of 50 milliliters and pump injected at 30 milliliters per minute onto a 45 mm ID radial compression column packed with 15μ, 100 Angstrom "DELTA PAK", (Waters) C18 stationary phase. The column was eluted initially at 20 mL/min with 60/40 A:B until the front running impurities had been eluted and increased to 55:45 at 40 mL/min and the elution continued. Fractions containing the desired product were pooled and concentrated in vacuo to remove most of the acetonitrile. The residue was lyophilized to obtain 1.5 grams (29 percent yield) of the nitrile intermediate (Seq. ID No. 15). The compound had the following spectral characteristics.

$^1$H-NMR (400 MHz, CD$_3$OD): δ 7.12 (d, 2H), 6.73 (d, 2H), 5.31 (d, 1H), 1.20 (d, 3H), 0.88 (t, 3H), 0.87 (d, 6H); Mass spectrum (FAB): 1054 (M+Li)

B. Preparation of Intermediate Propanolamine G-Ia (Seq ID No. 22)

To a solution of 2.1 grams (2 mmol) of the nitrile above prepared in 60 milliliters of methanol was added under nitrogen atmosphere, 1.04 grams (8 mmol, 4.0 molar eq.) of cobaltous chloride hexahydrate whereupon a purple solution formed. While the solution was stirred at room temperature, 1.51 grams (40 mmol, 20 molar eq) of sodium borohydride was added in portions over about 15 minutes. The addition of sodium borohydride produced a color change in the reaction medium to black which was accompanied by gas evolution. Gas evolution accompanied each of the additions. Stirring was continued overnight. An HPLC analysis carried out at this time using a 8 mm×10 cm "DELTA PAK" radial compression C18 column and eluting isocratically at 1.5 mL/min with 60/40 A:B [composition containing 0.1 percent acetic acid] with temperature at 40° C. and recording the refractive index at λ=210 nm. The analysis showed the ratio of amine:nitrile to be 64.7 to 15.2. The reaction mixture was diluted first with 20 milliliters of mobile phase, 70/30 A:B, [compositions containing 0.1 percent acetic acid], then acetic acid added to insure to a pH of about 5. The reaction mixture was then filtered through a pad of celite and the filter cake washed with methanol. The solution was then pump injected into a Waters 45 mm ID cm radial compression column packed 15μ, 100 A "DELTA PAK" C$_{18}$ stationary phase and eluted at 40.0 mL/min. The pure fractions were combined and concentrated in vacuo to remove most of the acetonitrile and then lyophilized to obtain 900 mg (42.8) percent of the product propanolamine, Compound G-Ia (Seq. ID No. 1 as the acid addition salt. HPLC analysis carried out on "ZORBAX" (DuPont) 4.9 mm×25 cm C8 column with isocratic elution at 1.5 mL/min with 45/55 A:B [compositions containing 0.1 percent TFA] at a temperature of 40° C. and λ=210 nm showed the product to be greater than 95 percent purity. The fractions containing the desired product were pooled, concentrated to obtain the propanolamine. The compound had the following spectral characteristics.

$^1$H-NMR (400 MHz, CD$_3$OD): δ 7.12 (d, 2H), 6.75 (d, 2H), 5.18 (d, 1H), 4.97 (d, 1H), 1.19 (d, 3H), 0.89 (t, 3H), 0.86 (d, 6H), Mass spectrum (FAB): 1058 (M+Li)

C. Preparation of Compound X-Ia 52 milligrams of the propanolamine compound prepared as above described as the acid additon salt, 900 milligrams of ethanolamine hydrochloride (200 equivalents), 10.9 miligrams (1.0 equivalent) of camphorsulfonic acid in 2.5 milliliters of dimethylsulfoxide (DMSO) and 0.5 milliliter of dimethylformamide were stirred together for about one week. An HPLC analysis taken at this time showed that about 80 percent conversion had occured. The mixture was then diluted with water and placed on a reverse phase silica gel column ("LICHROPREP" C18) packed in 85 percent A to 15 percent B to obtain 18.5 milligrams of the desired diamine as a substantially single product. The compound was purified by preparative HPLC to obtain 11.2 milligrams of purified product. The compound had the following spectral characteristics.

Mass spectrum (FAB): 1101 (M+Li) $^1$H NMR (400 MHz, CD$_3$OD): δ 7.12 (d, 2H), 6.77 (d, 2H), 5.18 (d, 1H), 3.14 (t, 2H), 3.09 (t, 2H).

EXAMPLE I-A

In a similar manner, the following compound was prepared:

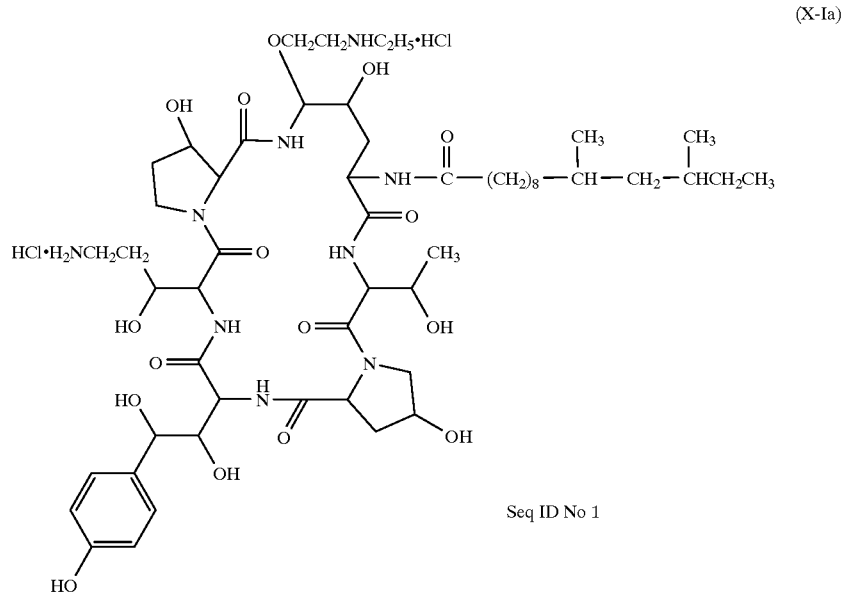

(X-Ia)

Seq ID No 1

Mass spectrum: (FAB) 1129 (M+Li).

EXAMPLE II

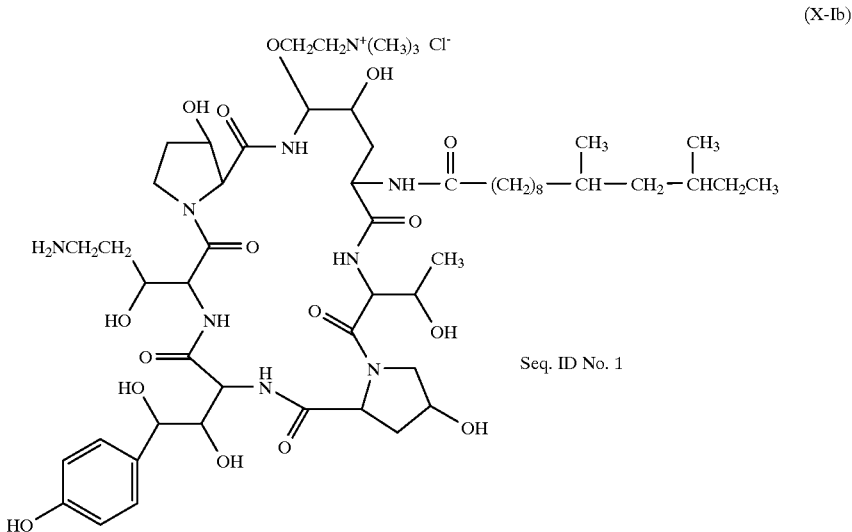

To a solution of 44 milligrams (42 μmol) of Compound G-Ia (Seq. ID No. 22) (prepared as described in Example I) and 100 equivalent of hydroxy ethyltrimethyl ammonium chloride is added 20 milligrams (2 eq) of camphorsulfonic acid and the resulting mixture stirred at room temperature until HPLC analysis indicated conversion of the starting material. The reaction mixture is then injected directly onto a "ZORBAX" (25 mm×25 cm) C8 column and eluted with 50/50 A:B at 8.0 mL/min. Pure fractions as determined by HPLC are pooled and lyophilized to the desired product Compound X-Ib (Seq ID No. 1), M.W.=1172.9 as the monochloride.

EXAMPLE III

A. Preparation of Intermediate Propanolamine J-Ia (Seq ID No. 22)

To a solution of 44 milligrams (42 μmol) of Compound G-Ia (Seq. ID No. 1) (prepared as described in Example I) in 1.0 milliliter of sieve dried DMF (13X, 3A molecular sieves) was added 4.5 milligrams (53 μmol) of sodium bicarbonate, followed by 250 milligrams of 4A sieves and finally 26 milliliters (417 μmol, 10 eq) of methyl iodide and the resulting solution was stirred at room temperature for 5 hours. At this time, 2.5 mg (30 μmol) of sodium bicarbonate and 26 milliliters (417 μmol) of methyl iodide were added and the resulting mixture stirred overnight at room temperature. The reaction mixture was then applied directly to a preparative HPLC column and eluted with 55/45 A:B at 8.0 ml/min. Pure fractions as determined by HPLC were pooled and lyophilized to obtain 17 milligrams (37 percent yield) of Compound H-Ia (Seq. ID No. 1). HPLC analysis indicated purity of 95.2 percent.

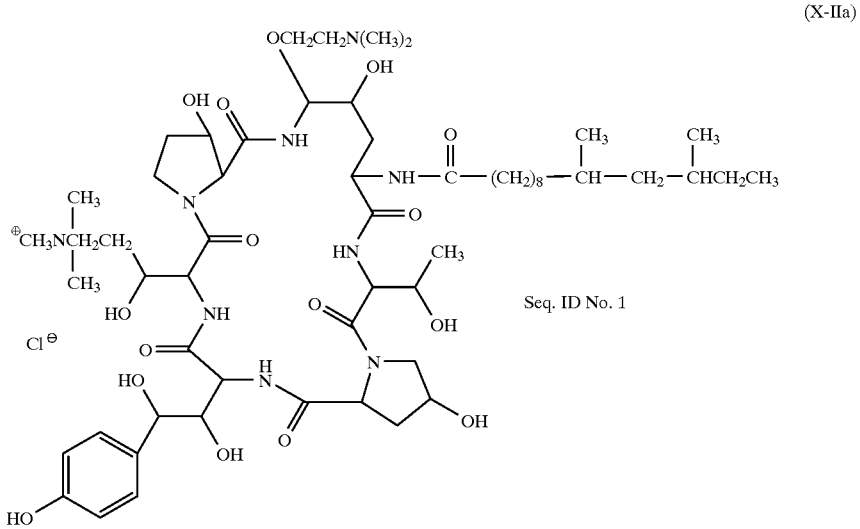

¹H-NMR (400 MHz, CD₃OD): δ 7.11 (d, 2H), 6.73 (d, 2H), 5.16 (d, 1H), 4.98 (d, 1H), 3.16 (s, 9H), 1.19 (d, 3H), 0.88 (t, 3H), 0.85 (d, 6H); Mass spectrum (FAB) 1094 (M+H).

B. Preparation of X-IIa

To a solution of 17 milligrams (17 μmol) of Compound J-Ia (Seq. ID No. 1) (prepared as described in Example I) and 100 equivalent of 2-N,N-dimethylaminoethanol hydrochloride in DMSO is added to milligrams (2 eq) of camphorsulfonic acid and the resulting mixture is stirred at room temperature until HPLC analysis indicated conversion of the starting material. The reaction mixture is then injected directly onto a "ZORBAX" (25 mm×25 cm) C8 column and eluted with 50/50 A:B at 8.0 mL/min. Pure fractions as determined by HPLC are pooled and lyophilized to the desired product Compound X-IIa (Seq ID No. 1). MW=1200.92 (as the monochloride).

EXAMPLE IV

To a solution of 44 milligrams (42 μmol) of Compound X-Ia (Seq. ID No. 1) (prepared as described in Example I) in 1.0 milliliter of sieve dried DMF (13X, 3A molecular sieves) is added 4.5 milligrams (53 μmol) of sodium bicarbonate, followed by 250 milligrams of 4A sieves and finally 26 microliters (417 μmol, 10 eq) of methyl iodide and the resulting solution is stirred at room temperature overnight. The reaction mixture is then applied directly to a preparative HPLC column and eluted with 40/60 A:B at 8.0 ml/min. Pure fractions, as determined by HPLC, are pooled and lyophilized to obtain Compound X-IIb, M.W. 1434.3 as the diiodide.

EXAMPLE V

In operations carried out as described in Example I and II, the following compounds in which $R_1$, $R_2$ and $R_4$ are OH, and the other substituents as set forth below are prepared:

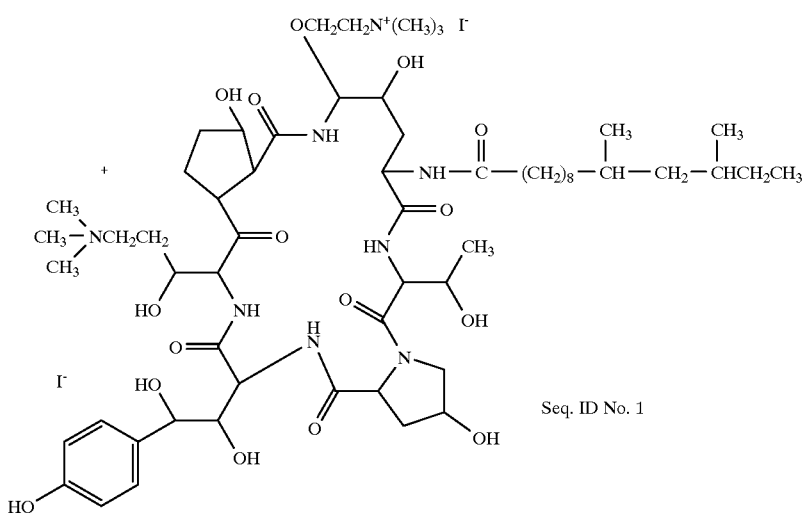

(X-IIb)

Seq. ID No. 1

| COMPOUND | $R_3$ | $R_5$ | $R_6$ | $R^I$ | $R^{II}$ | $R^{III}$ |
|---|---|---|---|---|---|---|
| V-A | OCH₂CH₂N(CH₃)CH₂CH₅ | H | CH₃ | DMTD* | CH₃ | CH₃ |
| V-B | OCH₂CH₂N⁺(CH₃)₂CH₂C₆H₅ I⁻ | H | CH₃ | DMTD | CH₃ | CH₃ |
| V-C | OCH₂CH₂N(CH₃)(C₄H₉-n) | H | CH₃ | DMTD | H | H |
| V-D | OCH₂CH₂CH₂NHCH₂C₆H₅ | H | CH₃ | DMTD | H | H |
| V-E | OCH₂CH₂NH₂ | CH₃ | CH₃ | DMTD | H | H |
| V-F | OCH₂CH₂N(CH₃)₂ | CH₃ | CH₃ | DMTD | H | H |
| V-G | OCH₂CH₂N⁺(CH₃)₃ I⁻ | CH₃ | CH₃ | DMTD | H | H |

*DMTD = 10,12-dimethyltridecyl
Compounds V-A through V-D are of Seq ID No. 1;
Compounds V-E through V-G are of Seq ID No. 2.

EXAMPLE VI

In operations carried out as described in Example III and IV, the following compounds in which $R_1$, $R_2$ and $R_4$ are OH , $R_6$ is $CH_3$ and the other substituents are as set forth below are prepared

| COM-POUND | $R_3$ | $R_5$ | $R^I$ | $R^{II}$ | $R^{III}$ | $R^{IV}$ |
|---|---|---|---|---|---|---|
| VI-A | $OCH_2CH_2NH_2$ | H | DMTD | $CH^3$ | $CH^3$ | $CH^3$ |
| VI-B | $OCH_2CH_2N$-$(C_2H_5)_3^+$ | H | DMTD | $CH^3$ | $CH^3$ | $CH^3$ |
| VI-C | $OCH_2CH_2NHCH_2$-$C_6H_5$ | $CH_3$ | DMTD | $CH^3$ | $CH^3$ | $CH^3$ |
| VI-D | $OCH_2CH_2CH_2N$-$(CH_3)_3^+Cl^-$ | $CH_3$ | DMTD | $CH^3$ | $CH^3$ | $CH^3$ |

Compounds VI-A and VI-B are of Seq ID No. 1;
Compounds VI-C and VI-D are of Seq ID No. 2.

EXAMPLE VII

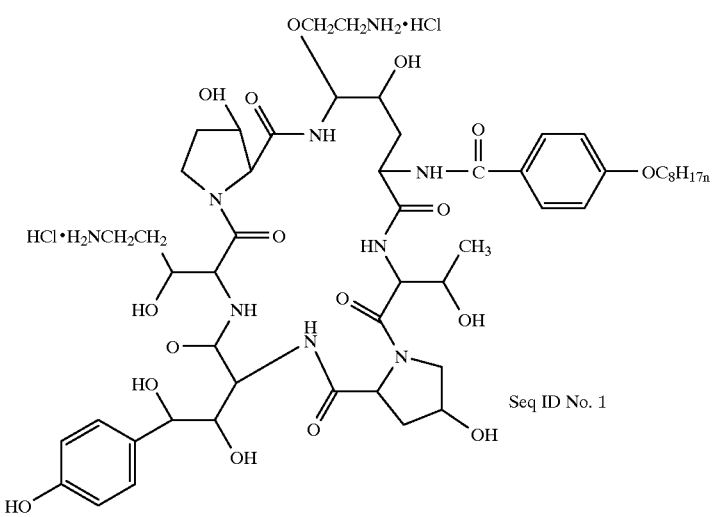

Seq ID No. 1

In a manner similar to that described in Example I, the following reaction was carried out:

A. Preparation of Intermediate Nitrile Compound (Seq. ID No. 15)

To a solution of 110 mg (0.104 mmol) of Compound E-1 (Seq. ID No. 21) (wherein $R_1$, $R_2$, $R_3$ and $R_4$ are OH, $R_5$ is H, $R_6$ is $CH_3$ and $R^I$ is

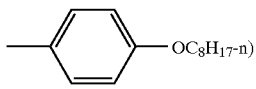

in sieve dried DMF under nitrogen was added in one portion, 59 mg (0.322 mmol) of cyanuric chloride. The reaction was allowed to proceed for 5.5 minutes when it was quenched by the addition of 1.35 milliliters of sodium acetate solution. HPLC analysis showed the product to starting material ratio to be 15.5:1. The reaction mixture was diluted with 2.0 milliliters of 50 percent aqueous acetonitrile and injected onto a radial compression C18 Δ-Pak column (15μ particle size, 100 Å pore size, 25 mm×50 cm). Elution was started as 12.0 mL/min with 75:25 $H_2O/CH_3CN$ both containing 0.1% TFA until all the DMF and other front running materials had been eluted. The gradient was then stepped up to 50:50 over the course of 30 minutes and pure fractions of the product was collected and combined. By lyophilization, 60 milligrams (55.5%) of product was obtained of >99.5% purity by HPLC (4.6 mm×25 cm "ZORBAX" C18; isocratic elution with 6:4 $H_2O/CH_3CN$ [both containing 0.1% TFA] flow rate=1.5 mL/min; temperature=40° C.; λ=210 nm; HPLC retention time=9.74 min). The compound had the following spectral characteristics.

$^1$H-NMR (400 MHz, $CD_3OD$): δ 7.82 (d, 2H), 7.12 (d, 2H), 6.94 (d, 2H), 6.75 (d, 2H), 5.37 (d, 1H), 2.86 (dd, 1H), 2.76 (dd, 1H), 2.44 (m, 1H), 2.29 (m, 1H), 1.21 (d, 3H), 0.9 (t, 3H). Mass Spectrum (FAB) 1048 (M+Li))

B. Preparation of the Intermediate Propanolamine Hydrochloride Compound (Seq. ID No. 22)

To a solution of 73 mg (0.070 mmol) of the nitrile above prepared in 3.0 mL in methanol was added 62 mg (0.476 mmol) of $CoCl_2.6H_2O$. The reaction mixture was stirred until all the $CoCl_2.6H_2O$ had dissolved. At this time 90 mg (2.38 mmol) of $NaBH_4$ was added in four portions over a course of 5 minutes with vigorous reaction and mixture turning black. After 5 hours, the reaction was seen to be substantially complete by HPLC and the reaction was quenched by the addition of 2N HCl (1.33 mL) and stirred until the dark color was discharged. The resulting solution was injected directly onto a HPLC column (radial compression C18 DELTA PAK column) and eluted at 12.0 mL/min with 75:25 $H_2O/CH_3CN$ (both containing 0.1% HOAc) until all the front running colored materials had been eluted. The gradient was then stepped up to 70:30 and pure fractions of the product were collected, combined and lyophilized to obtain 21 milligrams (29% yield) of product as hydrochloride salt of greater than 99.5 percent purity by HPLC (using isocratic elution as detailed above). HPLC retention time= 6.46 minutes. The compound had the following spectral characterictics.

$^1$H NMR (400 MHz, $CD_3OD$) δ 7.82 (d, 2H), 7.12 (d, 2H), 6.69 (d, 2H), 6.75 (d, 2H), 5.27 (d, 1H), 5.10 (d, 1H), 2.45 (m, 1H), 2.29 (m, 1H), 1.21 (d, 3H), 0.9 (t, 3H). Mass Spectrum (FAB): 1052 (M+Li)

C. Preparation of Bisamine Compound of formula X-Ia (Seq ID No 1)

To a solution of 56 mg of ethanolamine hydrochloride in 120 μL was added 15 mg (0.143 mmol) of the propanolamine prepared in a manner similar to that described in Part B of Example VII. Stirring was continued and when a complete solution was obtained, 3.6 μL of HCl in dioxane was added. The reaction mixture was then capped and stirred for six days at room temperature. At the end of this time, the reaction mixture was injected onto a "ZORBAX" C8 column and elution started with 8:2 $H_2O/CH_3CN$ (containing 0.1% TFA) at 4.0 mL/min. Then when all the DMSO and other front running material had been eluted the gradient was stepped up to 75:25. After three column volumes, the gradient was again stepped up to 7:3. Appropriate fractions after analysis by HPLC were combined and lyophilized to obtain 4.8 milligrams (31 percent yield) of product of greater than 99% purity by HPLC "ZORBAX" C18 with isocratic elution with 65:35 $H_2O/CH_3CN$, $\lambda=210$; HPLC retention time 7.27 minutes. The product had the following spectral properties:

$^1$H NMR (400 MHz; $CD_3OD$) δ 7.82 (d, 2H), 7.12 (d, 2H), 6.98 (d, 2H), 6.75 (d, 2H), 5.24 (d, 1H), 4.03 (t, 2H), 3.64 (m, 1H), 2.45 (m, 1H), 1.18 (d, 3H), 0.91 (t, 3H). Mass spectrum (FAB) 1095 (M+Li)

EXAMPLE VIIa

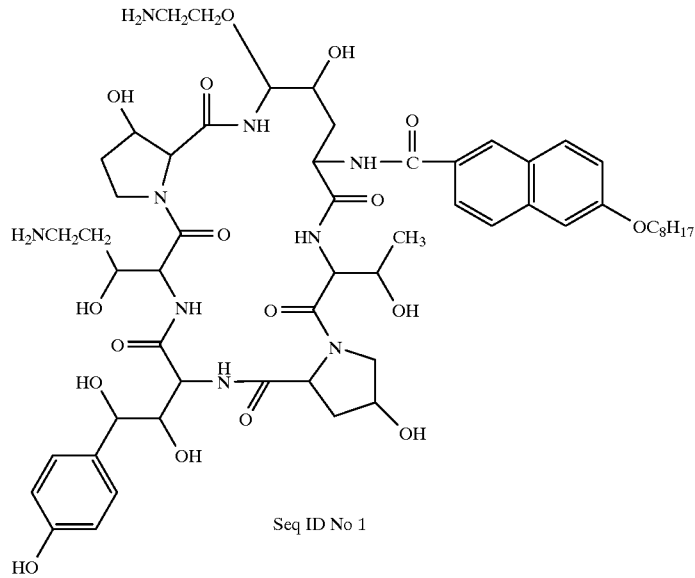

Seq ID No 1

In a similar fashion, the above compound having a molecular weight of 1138 may be prepared.

EXAMPLE VIII

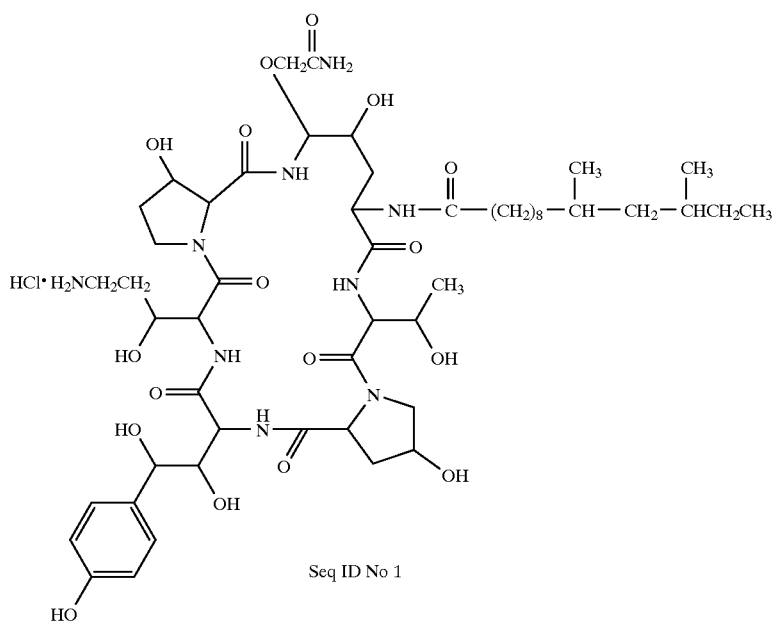

Seq ID No 1

To 315 mg (0.3 mmol) of the propanolamine hydrochloride compound prepared in Part B of Example I and 901 mg (12 mmol) of glycolamide in 2.5 mL DMSO was added 75 μL 4M HCl in dioxane. After 72 hours, the reaction mixture was injected onto a radial compression module packed with "DELTA PAK" C18 stationary phase. Elution was started with 7:3 $H_2O$ $CH_3CN$ at 15.0 mL/min. When all the DMSO and other front running materials had been eluted the gradient was increased to 6:4, fractions collected, analyzed by HPLC, combined and lyophilized to obtain 143 mg (44 percent yield) of 99.5 percent purity by HPLC ("ZORBAX" C18 using previous conditions). HPLC retention time=7.42. The product (Seq ID No 1) had the following spectral properties.

$^1$H NMR (400 MHz; $CD_3OD$) δ 7.12 (d, 2H), 6.75 (d, 2H), 5.12 (d, 1H), 4.97 (d, 1H), 3.06 (t, 2H), 2.44 (m, 1H), 1.16 (d, 3H). Mass Spectrum (FAB) 1114 (M+Li)

EXAMPLE IX

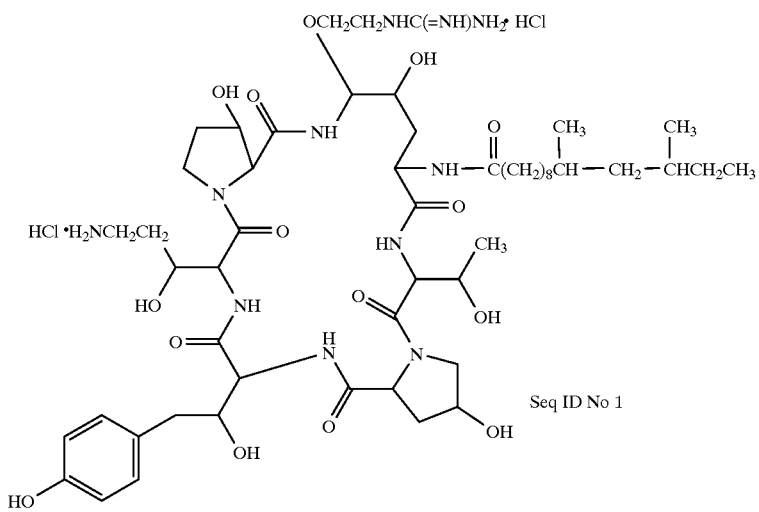

(X-Ia)

Seq ID No 1

The above compound having a molecular weight of 1310 may be prepared in a manner similar to that described in Part C of Example I.

EXAMPLE X

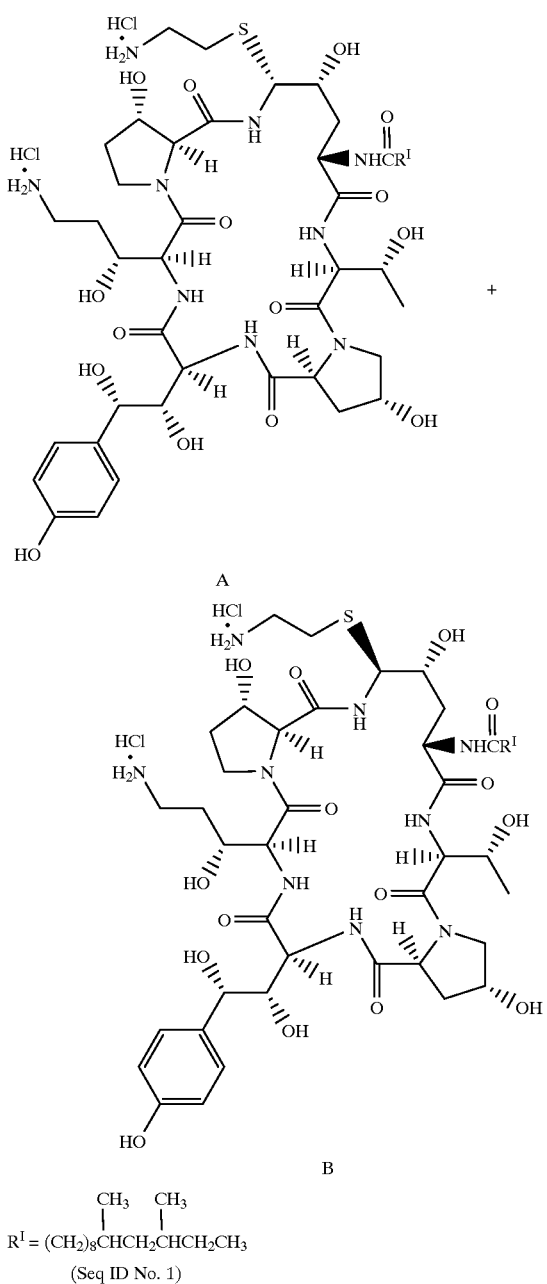

(Seq ID No. 1)

700 milligrams (0.645 mmol) of Compound G hydrochloride (Seq ID No 22) 7.3 grams (64.5 mmol) 150 milligrams (0.645 mmol) of 2-aminoethanethiol and 150 milligrams (0.645 mmol) of (1S)-(+)-10 camphorsulfonic acid were stirred in 25 milliliters of anhydrous N,N-dimethylformamide at ambient temperature for four days. An HPLC determination of the reaction mixture (ZORBAX C8, 4.6 mm×25 cm, 50:50 $CH_3CN/H_2O$ (0.1% trifluoroacetic acid) at 1.5 mL/min, UV 277 nm) indicated the presence of three products, a degradation product and isomeric thio-ether and epithioether products A and B above. The reaction mixture was diluted with 75 milliliters of water and flash chromatographed eluting with 10–50 percent acetonitrile/water (0.1% trifluoroacetic acid). The eluate fractions were concentrated and lyophilized to obtain crude products. The products were purified by preparative HPLC on "ZORBAX" $C_8$ column using 35–55 percent acetonitrile/water as eluant to obtain Products A and B above as ditrifluoroacetate salts. The trifluoroacetate salts were converted to dihydrochloride salts using AG2-X8(Cl$^-$) resin (product of Bio Rad), and eluting with water to obtain 107 milligrams of A as dihydrochloride and 132 milligrams of B as dihydrochloride. The spectral properties were as follows:

A.2HCl:

$^1$H NMR (400 MHz, $CD_3OD$) δ 1.17 (d, J=6.2 Hz), 2.9(m), 3.06 (t, J=7.2 Hz), 3.20 (t, J=6.7 Hz), 4.91 (d, J=5.8 Hz), 4.99 (d, J=3.4 Hz), 5.27 (d, J=2.07 Hz), Mass Spectra: FAB (Li) m/z 1117 (MH+Li)$^+$ B.2HCl $^1$H NMR (400 MHz, $CD_3OD$) δ 4.95 (d, J=3.9 Hz); Mass Spectra: FAB(Li), m/z 1117 (MH+Li)$^+$

EXAMPLE XI

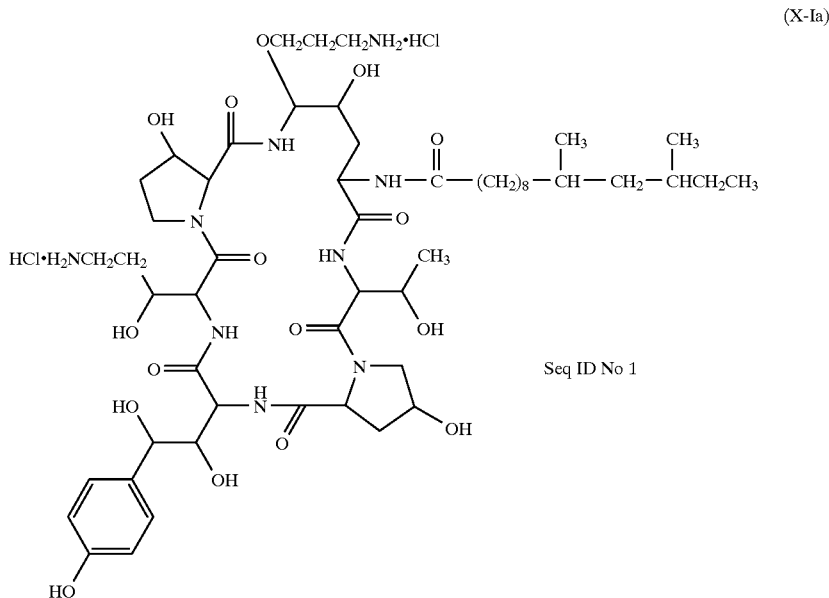

(X-Ia)

Seq ID No 1

A solution of 510 milligrams (0.469 mmol) of G-I (Seq ID No 22), 2.42 grams (11.6 mmol) of 3-(N-benzyloxycarbonylamino)propanol, and 109 milligrams (0.469 mmol) of (1S)-(+)-10-camphorsulfonic acid in 10 mL anhydrous dioxane, 2 mL anhydrous DMF and 1 mL DMSO was stirred at 25° C. for a period of 24 hours. HPLC analysis ("ZORBAX" C8, 4.6 mm×25 cm; 60% $CH_3CN/H_2O$ [0.1% TFA]) at 2 mL/min; 210 and 277 nm) indicated conversion to a less polar product ($t_R$=5.39 min). The reaction mixture was neutralized by the addition of 480 mL of 1M $NaHCO_3$ and diluted with 13 mL water. Reverse phase flash chromatography ("LICHROPREP" RP-18 (40–63 μm), 20 g) eluting with 40–60% $CH_3CN/H_2O$ in 10% step gradient followed by lyophilization of the appropriate fractions to obtain a CBZ protected Compound X-I ($R_1$, $R_2$, $R_4$=OH; $R_5$=H; $R_6$=$CH_3$; $R'$=DMTD and $R_3$ is $O(CH_2)_3NHCBZ$).

A solution of 300 mg (80% pure 0.188 mmol corrected) of above compound in 10 mL of acetic acid was hydrogenated under balloon pressure in the presence of 10% Pd/C (200 mg) for a period of 3 hours. HPLC analysis ("ZORBAX" C8, 4.6 mm×25 cm; 50% $CH_3CN/H_2O$ [0.1% TFA] at 1.5 mL/min; λ-210 and 277 nm) indicated complete conversion to a more polar product ($t_R$=3.47 min). The reaction mixture was filtered to remove the catalyst, rinsing with methanol and the filtrate concentrated in vacuo. The residue was purified by preparative HPLC ("ZORBAX" C8, two 21.2 mm×25 cm; 35% $CH_3CN/H_2O$ [0.1% TFA] at 15 mL/min; λ-220 nm), the appropriate fractions were lyophilized to obtain 58 milligrams of product of above structure of purity >98% (by HPLC). The material was dissolved in water and placed on AG2-X8 (Cl⁻) column (BioRad, bed volume 2 mL) and eluted with 10 milliliters of water. The eluate was lyophilized to obtain 53 milligrams of a dihydrochloride of the product.

Mass spectrum: (FAB) 1115 (M+Li).

EXAMPLE XII

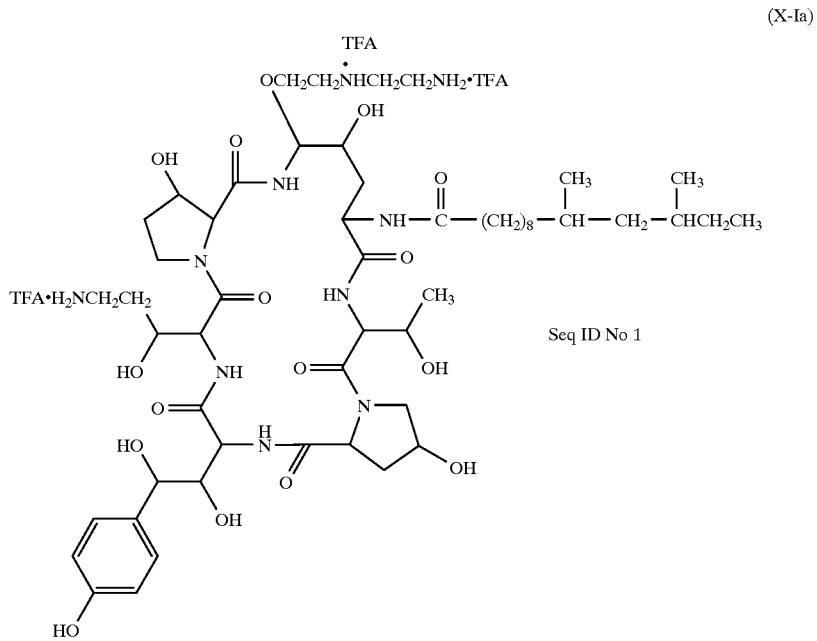

(X-Ia)

Seq ID No 1

In a manner similar to that described in Example XI, the above compound was prepared. The compound had the following spectral properties.

$^1$H NMR (400 MHz; CD$_3$OD) δ 7.12 (d, 2H), 6.76 (d, 2H), 5.16 (d, 1H), 4.98 (d, 1H), 3.95 (dd, 1H), 3.07 (t, 2H), 2.44 (m, 1H), 1.18 (d, 3H). Mass spectrum (FAB) 1143 (M+Li).

EXAMPLE XIIa

In a similar manner, the following compound was prepared:

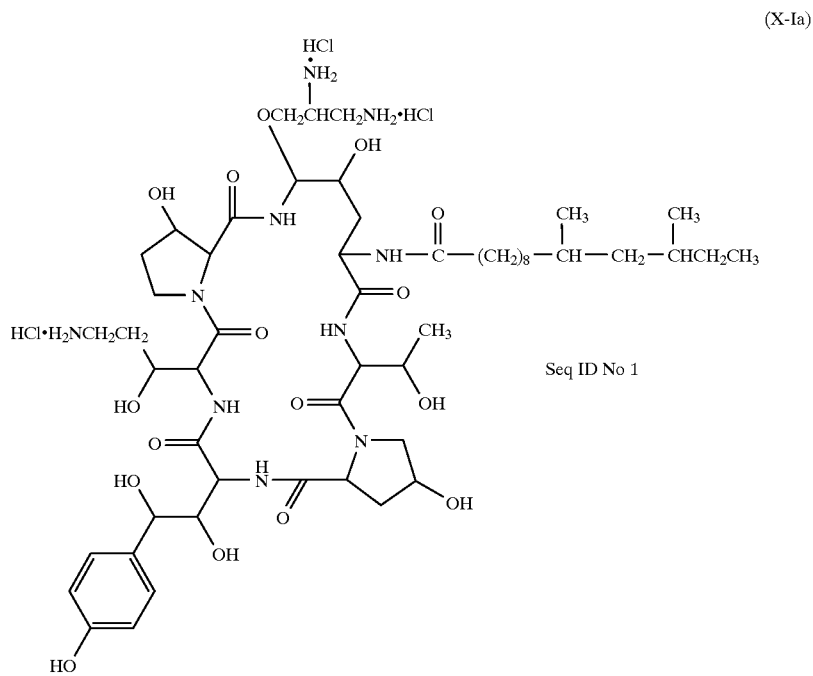

(X-Ia)

Seq ID No 1

The mass spectrum of the compound was as follows:
Mass spectrum: (FAB) 1130 (M+Li).

EXAMPLE XIII

In a manner similar to that described in Example X, the following (X-Ia) compounds may be prepared in which $R_6$ is $CH_3$, $R^I$ is $-C_6H_4OC_8H_{17}$ and $R^{II}$ and $R^{III}$ are $CH_3$:

| $R_1$ | $R_2$ | $R_3$* | $R_4$ | $R_5$ | Seq ID |
|---|---|---|---|---|---|
| OH | H | $S(CH_2)_2NH_2$ | OH | $CH_3$ | 4 |
| H | H | $O(CH_2)_2N(CH_2)_5$ | H | $CH_3$ | 5 |
| OH | OH | $O(CH_2)_2NHCH_2C_6H_5$ | OH | OH | 6 |

*as dihydrochloride salt

EXAMPLE XIV

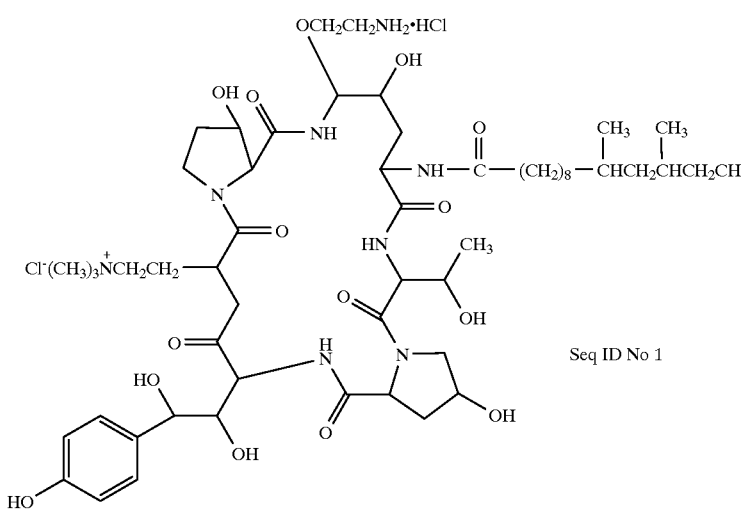

Seq ID No 1

To a solution of 1.25 grams (12.8 mmol) of ethanolamine hydrochloride in 2.5 mL of dry DMSO was added 350 mg (0.32 mmol) of a quaternized propanolamine compound ($R_1$, $R_2$, $R_3$ and $R_4$ are OH, $R_5$ is H, $R_6$ is $CH_3$, $R^I$ is dimethyltridecyl, $R^{II}$, $R^{III}$ and $R^{IV}$ are methyl with $Cl^-$ counterion) and the stirring continued until complete solution was obtained. 80 microliters of 4M HCl in dioxane was added and the reaction mixture capped and stirred for four days at room temperature. After four days another 80 microliter aliquot of 4M HCl in dioxane was added and the resulting mixture stirred overnight. The mixture was then injected into a radial compression module with "DELTA PAK" C18 (15μ particle size, 100A pore size) stationary phase and elution started with 7:3 water/acetonitrile [0.1% TFA] at 15.0 mL/min. When DMSO and other front running materials had been eluted the gradient was stepped up to 65:35. Fractions were collected, analyzed by HPLC, appro-priate fractions combined and lyophilized to obtain 50 milligrams of product of 99 percent purity by HPLC ("ZORBAX" C18; isocratic elution with 55:45 water/acetonitrile (0.1% TFA) at flow rate of 1.5 mL/min; 40° C.; λ=210 nm; HPLC retention time=6.62 min.) The product had the following spectral properties:

$^1$H NMR (400 MHz, $CD_3OD$) δ 7.12 (d, 2H), 6.75 (d, 2H), 5.15 (d, 1H), 5.98 (d, 1H), 3.19 (s, 9H), 2.44 (m, 1H), 2.25 (m, 1H), 1.18 (d, 3H). Mass Spectrum (FAB) 1137 (M+1)

(X-IIa)

EXAMPLE XV

In operations carried out in a similar manner, the following (X-IIa) compounds may be prepared in which $R_1$, $R_2$ and $R_4$ are hydroxyl, $R_6$ is methyl and $R^{II}$, $R^{III}$ and $R^{IV}$ are all $C_2H_5$ and the anion is $Cl^-$.

| $R_3$ | $R_5$ | R-1 | Seq. ID No. |
|---|---|---|---|
| $OCH_2CH(NHCH_3)CH_2OH$ | H | $C_6H_4OC_8H_{17}$ | 1 |
| $S(CH_2)_2NH_2$ | OH | $C_{10}H_6OC_6H_{13}$ | 6 |
| $SCH_2CONH_2$ | OH | $C_6H_4OC_8H_{17}$ | 6 |
| $O(CH_2)_3C(CH_3)_2NH_2$ | $CH_3$ | DMTD | 2 |

EXAMPLE XV

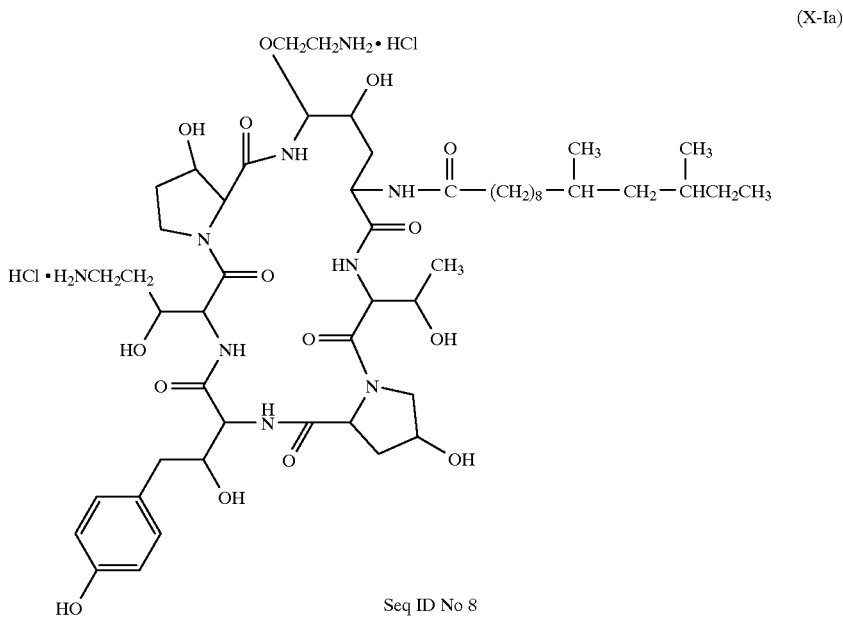

(X-Ia)

Seq ID No 8

To 260 milligrams (0.223 mmol) of Compound X-Ia in 5 mL of TFA under an atmosphere of nitrogen was added 70 milligrams (1.11 mmol) of sodium cyanoborohydride at once resulting in a vigorous gas evolution. After 2 minutes the mixture was diluted with 50 milliliters of water. An HPLC analysis ("ZORBAX" C18; 4.6 mm×25 cm; 50 percent $CH_3CN/H_2O$ [0.1% TFA] at 1.5 mL/min; $\lambda$=210 and 277 nm) indicated complete conversion to a slightly less polar product ($t_R$=3.46 min). Two volumes of methanol was added and the reaction mixture concentrated in vacuo, and lyophilized. The lyophilizate was purified by preparative HPLC ("ZORBAX" C18, two 21.2 mm×25 cm columns, 30–35% $CH_3CN/H_2O$ [0.1% TFA] at 15 mL/min; $\lambda$=220 nm). The appropriate fractions were combined and lyophilized to obtain 115 mg of the above compound as a di-trifluoroacetate (purity >98 percent by HPLC). The trifluoroacetate was dissolved in water and placed in AG2-X8 ($Cl^-$) (BioRad) column (bed volume 2 mL) and eluted with water and lyophilized to obtain 100 milligrams of the dihydrochloride.

Mass spectrum: (FAB) 1085 (M+Li).

EXAMPLE XVII 1000 hard gelatin capsules each containing 500 mg of Compound X-Ib are prepared from the following formulation:

| Compound | Grams |
| --- | --- |
| Compound X-Ib | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE XVIII

An aerosol composition may be prepared having the following formulation:

| | Per Canister |
| --- | --- |
| Compound X-Ia | 24 mg |
| Lecithin NF Liquid Concentrated | 1.2 mg |
| Trichlorofluoromethane, NF | 4.026 g |
| Dichlorodifluoromethane, NF | 12.15 g |

EXAMPLE XIX 250 milliliters of an injectible solution may be prepared by conventional procedures having the following formulation:

| Dextrose | 12.5 g |
| --- | --- |
| Water | 250 ml |
| Compound X-IIa | 400 mg |

The ingredients are blended and thereafter sterilized for use.

Preparation of Starting Materials:

The starting materials for the compounds are natural products or derivatives of natural products.

The following compounds are natural products produced by cultivating an appropriate organism in nutrient medium as hereinafter described.

E-1 may be produced by cultivating *Zalerion arboricola* ATCC 20868 in a nutrient medium enriched in mannitol as the primary source of carbon as described in U.S. Pat. No. 5,021,341, Jun. 4, 1991.

E-2 may be produced by cultivating *Zalerion arboricola* ATCC 20868 in nutrient medium as described in U.S. Pat. No. 4,931,352, Jun. 5, 1990 or in nutrient medium enriched in glycerol as described in U.S. Pat. No. 4,968,608, Nov. 6, 1990.

E-2 nucleus with a different R may be produced by cultivating *Acrophialophora limonispora* in nutrient medium as described in U.S. Pat. No. 4,173,629.

E-3 and E-7 may be produced by cultivating Cryptosporiopsis ATCC 20594 in nutrient medium as described by Pache et al in 13th ICC (1983), PS 4.8/3, Part 115, Abstract No. 10 and PCT WO 82/00587.

E-4, E-5 and E-6 may be produced by cultivating *Zalerion arboricola* ATCC 20868 in nutrient medium.

Starting materials in which $R^I$ is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as also described in Experentia 34, 1670 (1978) or U.S. Pat. No. 4,293,482, and thereafter recovering the deacylated cyclopeptide, and acylating the deacylated cyclopeptide by mixing together with an appropriate active ester $R^ICOX$ to obtain Compound E with the desired acyl group using conventional procedures. Methods are also described in U.S. Pat. Nos. 4,287,120 and 4,293,489.

What is claimed is:

1. A compound selected from the group consisting of:

(A) an amine (Seq ID Nos 1–7, 29) represented by the formula

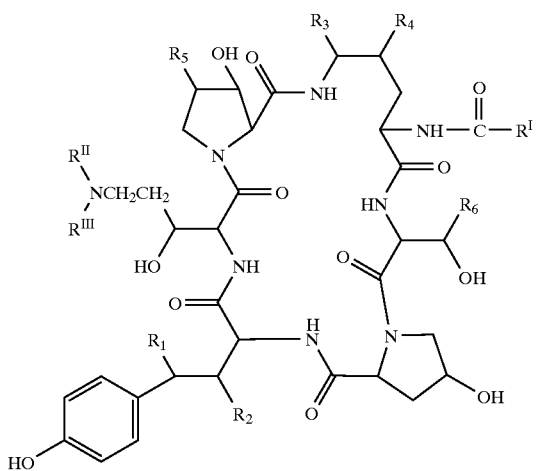

or its acid addition salt, and (B) a quaternary ammonium salt (Seq ID Nos 1–7, 29) represented by the formula:

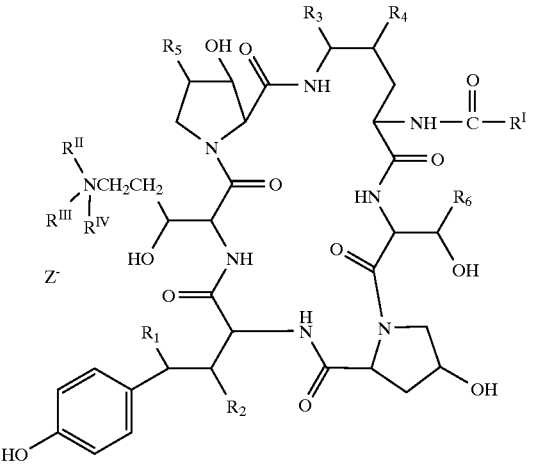

wherein
$R_1$ is H or OH
$R_2$ is H or OH
$R_3$ is $QC_nH_{2n}NR^VR^{VI}$, $QC_nH_{2n}NR^VR^{VI}R^{VII+}Y^-$, or $Q(CH_2)_{1-3}CR^{VIII}R^{IX}NHR^X$
$R_4$ is H or OH
$R_5$ is H, OH or $CH_3$
$R_6$ is H or $CH_3$
$R^I$ is $C_9$–$C_{21}$ alkyl, $C_9$–$C_{21}$ alkenyl, or $C_1$–$C_{10}$ alkoxyphenyl, or $C_1$–$C_{10}$ alkoxynaphthyl
$R^{II}$ is H, $C_1$–$C_4$ alkyl or benzyl $R^{III}$ is H, $C_1$–$C_4$ alkyl or benzyl or $R^{II}$ and $R^{III}$ together is —$(CH_2)_4$— or —$(CH_2)_5$—

$R^{IV}$ is $C_1$–$C_4$ alkyl $R^V$ is H, $C_1$–$C_4$ alkyl or benzyl $R^{VI}$ is H, $C_1$–$C_4$ alkyl or benzyl, or $R^V$ and $R^{VI}$ together is —$(CH_2)_4$— or —$(CH_2)_5$—

$R^{VII}$ is H, $C_1$–$C_4$ alkyl $R^{VIII}$ is H, $(CH_2)_mH$, $(CH_2)_mOH$, $(CH_2)_mNH_2$ or COX wherein X is $NH_2$, OH or $O(CH_2)_mH$ $R^{IX}$ is H, $(CH_2)_mH$ or together with $R^{VIII}$ is =O(carbonyl);

$R^X$ is H (except when $R^{VIII}$ and $R^{IX}$ are H), C(=NH)$NH_2$, C(=NH)$(CH_2)_{0-3}H$, CO$(CH_2)_{0-3}H$, CO$(CH_2)_m$ $NH_2$, $(CH_2)_{2-4}OH$ or $(CH_2)_{2-4}NH_2$ Q is O or S Z is an anion of a pharmaceutically acceptable salt Y is an anion of a pharmaceutically acceptable salt, and each m is independently an integer of from 1 to 3 inclusive, n is an integer of from 2 to 4 inclusive.

2. A compound according to claim 1 having the formula (Seq ID No 29)

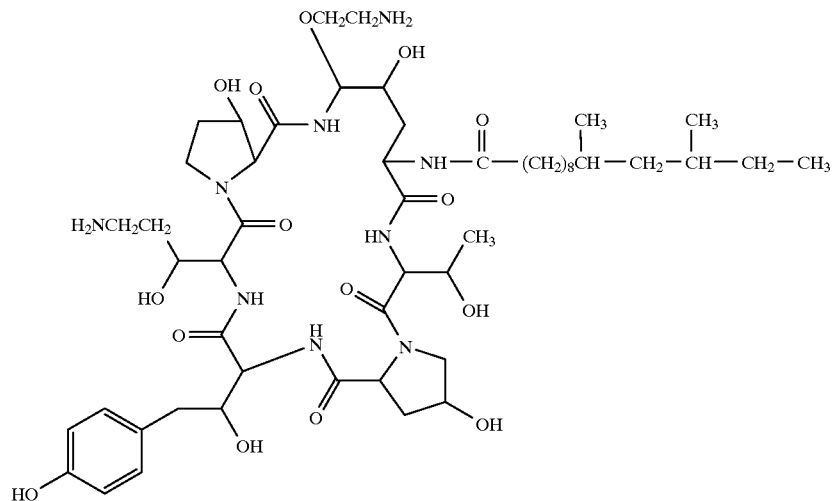

3. A compound according to claim 1 having the formula (Seq ID No 1)

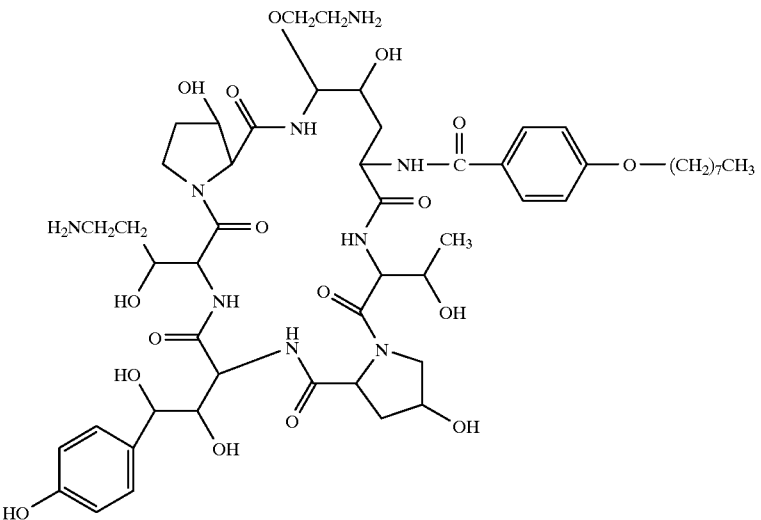

4. A compound according to claim 1 having the formula (Seq ID No. 1)

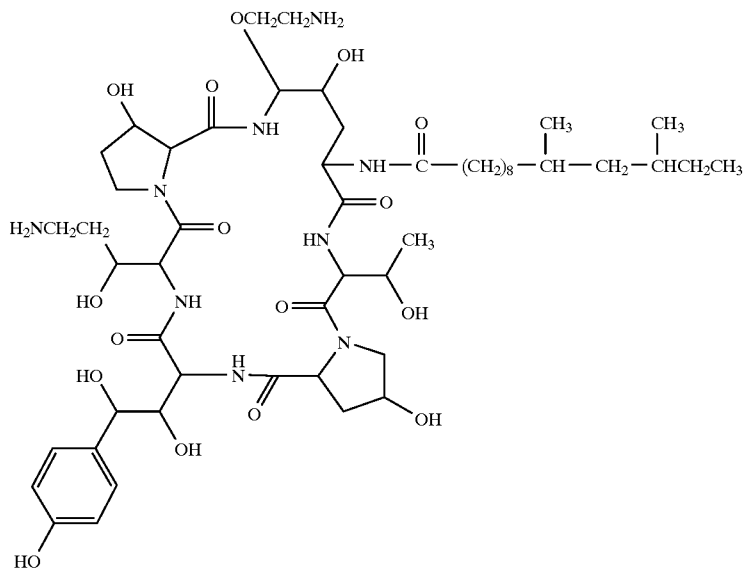
5. A compound according to claim 1 having the formula (Seq ID No. 1)
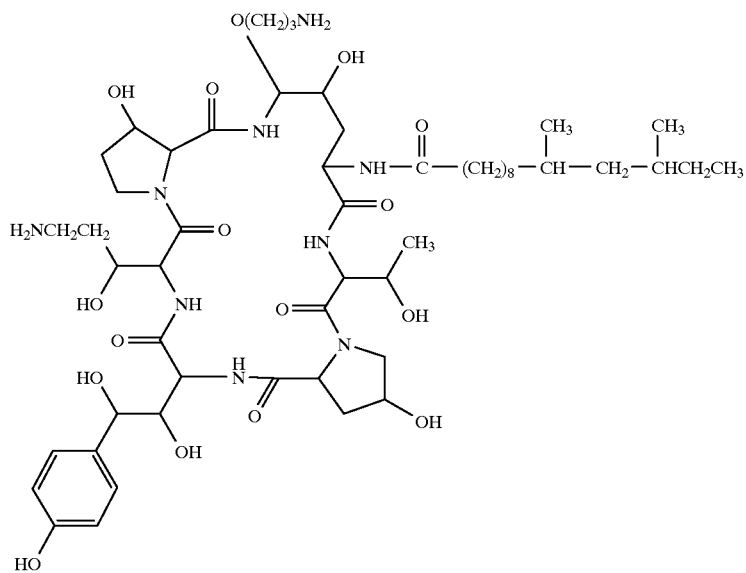
6. A compound according to claim 1 having the formula (Seq ID No. 1)

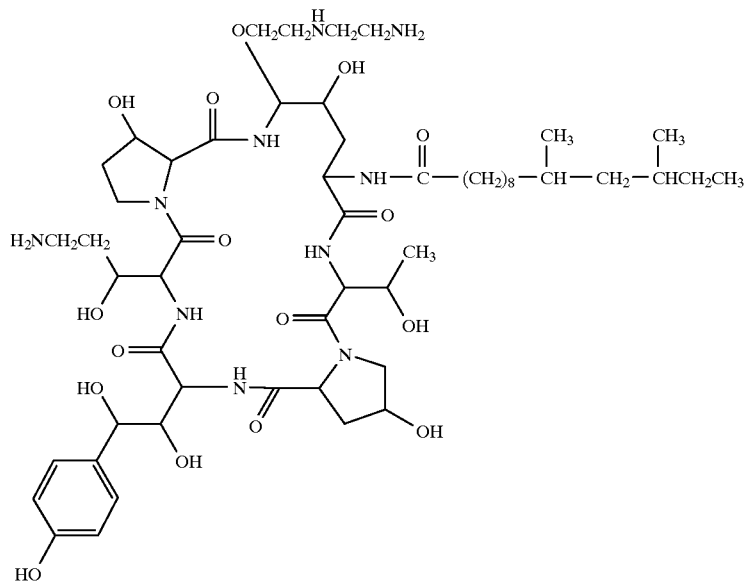
7. A compound according to claim 1 having the formula
(Seq ID No. 1)
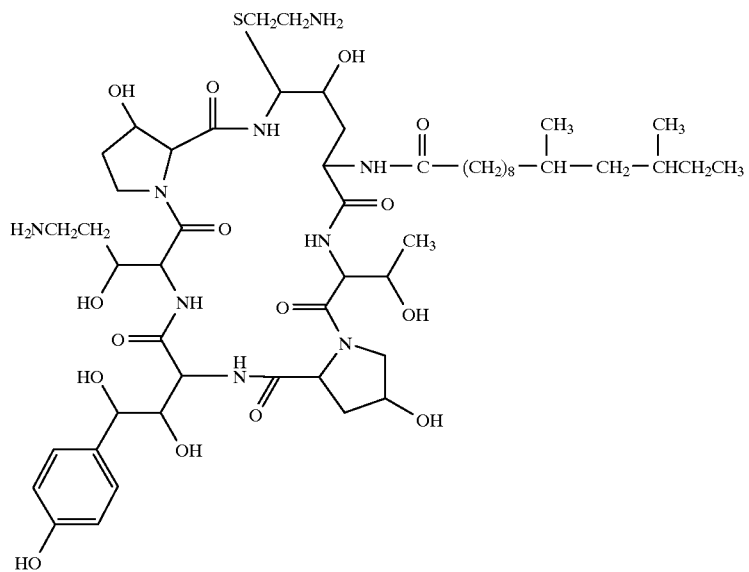
8. A compound according to claim 1 having the formula
(Seq ID No. 1)

9. A compound according to claim 1 having the formula (Seq ID No. 1)
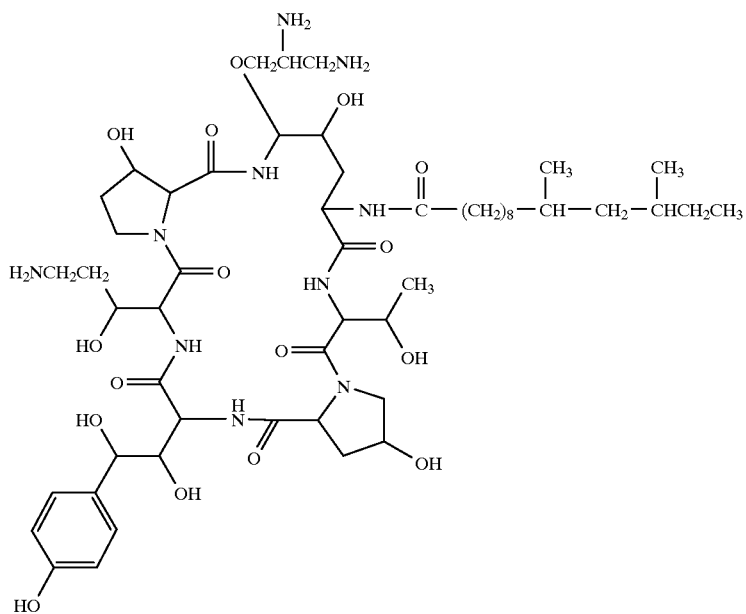
10. A compound according to claim 1 having the formula (Seq ID No. 1)
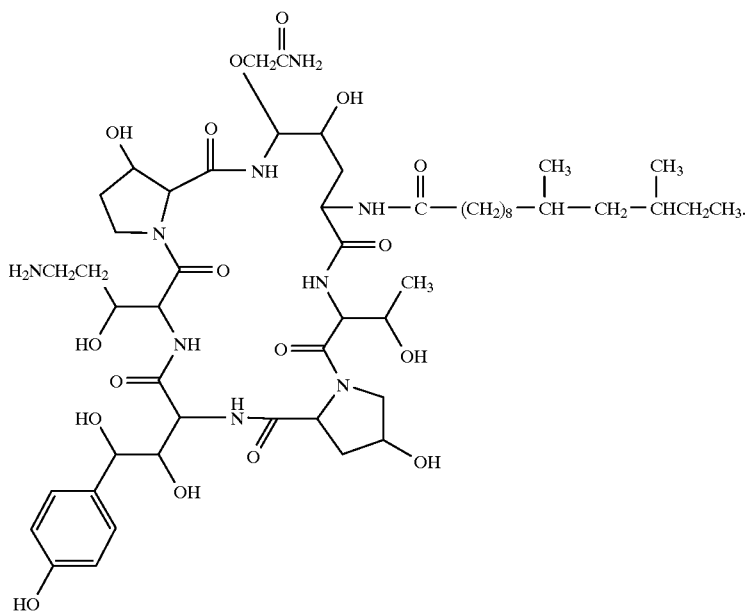

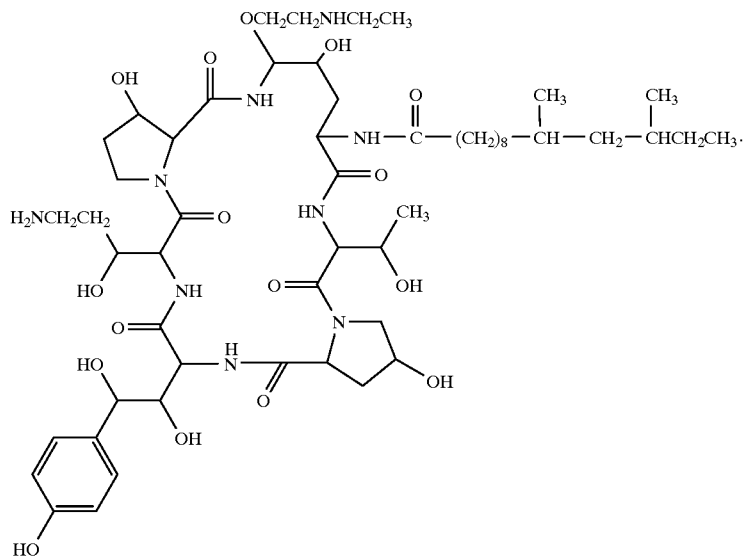
11. A compound according to claim 1 having the formula (Seq ID No 1)
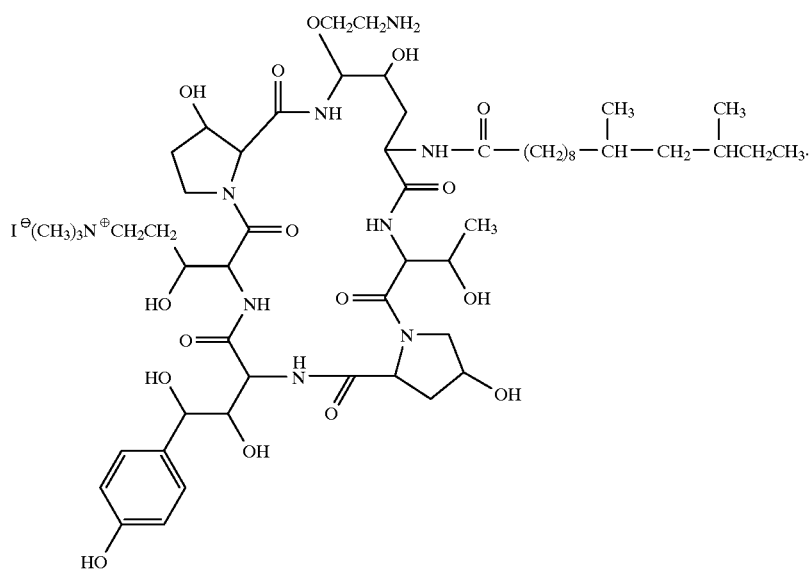
12. A compound according to claim 1 wherein the compound has the formula (Seq. ID No. 1)

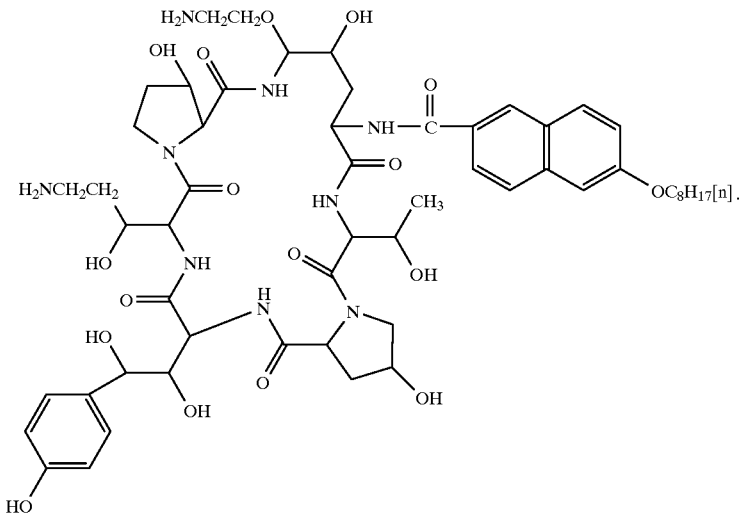
13. An antibiotic composition comprising therapeutic amount of a compound of claim 1 in a pharmaceutically acceptable carrier.
14. A composition according to claim 13 in unit dosage form wherein the compound of claim 1 is present in an amount of 10 milligrams to 200 milligrams.
* * * * *

UNITED STATES PATENT AND TRADEMARK OFFICE
CERTIFICATE OF CORRECTION

PATENT NO. : 6,030,944
DATED : February 29, 2000
INVENTOR(S) : Frances Aileen Bouffard, James F. Dropinski and Robert A. Zambias It is certified that error appears in the above-identified patent and that said Letters Patent is hereby corrected as shown below:

At claim 1, column 54, line 61 should read as follows:

-- $R_5$ is H -- .

Signed and Sealed this

Twelfth Day of December, 2000

Attest:

Q. TODD DICKINSON

Attesting Officer

Director of Patents and Trademarks

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
      (A) LENGTH: 6
      (B) TYPE: AMINO ACID
      (C) STRANDEDNESS: Not Relevant
      (D) TOPOLOGY: CIRCULAR (ii) MOLECULE TYPE:
      (A) DESCRIPTION: PEPTIDE (xi) SEQUENCE DESCRIPTION: SEQ ID NO: 1:

Xaa Thr Xaa Xaa Xaa Xaa
1             5

(2) INFORMATION FOR SEQ ID NO: 2:

(i) SEQUENCE CHARACTERISTICS:
      (A) LENGTH: 6
      (B) TYPE: AMINO ACID
      (C) STRANDEDNESS: Not Relevant
      (D) TOPOLOGY: CIRCULAR (ii) MOLECULE TYPE:
      (A) DESCRIPTION: PEPTIDE (xi) SEQUENCE DESCRIPTION: SEQ ID NO: 2:

Xaa Thr Xaa Xaa Xaa Xaa
1             5

(2) INFORMATION FOR SEQ ID NO: 3:

(i) SEQUENCE CHARACTERISTICS:
      (A) LENGTH: 6
      (B) TYPE: AMINO ACID
      (C) STRANDEDNESS: Not Relevant
      (D) TOPOLOGY: CIRCULAR (ii) MOLECULE TYPE:
      (A) DESCRIPTION: PEPTIDE (xi) SEQUENCE DESCRIPTION: SEQ ID NO: 3:

Xaa Ser Xaa Xaa Xaa Xaa
1             5

(2) INFORMATION FOR SEQ ID NO: 4:

(i) SEQUENCE CHARACTERISTICS:

(A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 4:

Xaa Thr Xaa Xaa Xaa Xaa
1               5

(2) INFORMATION FOR SEQ ID NO: 5:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 5:

Xaa Thr Xaa Xaa Xaa Xaa
1               5

(2) INFORMATION FOR SEQ ID NO: 6:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 6:

Xaa Thr Xaa Xaa Xaa Xaa
1               5

(2) INFORMATION FOR SEQ ID NO: 7:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 7:

Xaa Ser Xaa Xaa Xaa Xaa
1               5

(2) INFORMATION FOR SEQ ID NO: 8:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 8:

Xaa Thr Xaa Xaa Xaa Xaa
1               5

(2) INFORMATION FOR SEQ ID NO: 9:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 9:

Xaa Thr Xaa Xaa Xaa Xaa
1           5

(2) INFORMATION FOR SEQ ID NO: 10:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 10:

Xaa Ser Xaa Xaa Xaa Xaa
1           5

(2) INFORMATION FOR SEQ ID NO: 11:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 11:

Xaa Ser Xaa Xaa Xaa Xaa
1           5

(2) INFORMATION FOR SEQ ID NO: 12:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 12:

Xaa Thr Xaa Xaa Xaa Xaa
1           5

(2) INFORMATION FOR SEQ ID NO: 13:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 13:

Xaa Thr Xaa Xaa Xaa Xaa
1               5

(2) INFORMATION FOR SEQ ID NO: 14:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 14:

Xaa Ser Xaa Xaa Xaa Xaa
1               5

(2) INFORMATION FOR SEQ ID NO: 15:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 15:

Xaa Thr Xaa Xaa Xaa Xaa
1               5

(2) INFORMATION FOR SEQ ID NO: 16:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 16:

Xaa Thr Xaa Xaa Xaa Xaa
1               5

(2) INFORMATION FOR SEQ ID NO: 17:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 17:

Xaa Ser Xaa Xaa Xaa Xaa
1               5

(2) INFORMATION FOR SEQ ID NO: 18:

(i) SEQUENCE CHARACTERISTICS:
            (A) LENGTH: 6
            (B) TYPE: AMINO ACID

```
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 18:

Xaa Thr Xaa Xaa Xaa Xaa
1               5

(2) INFORMATION FOR SEQ ID NO: 19:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 19:

Xaa Thr Xaa Xaa Xaa Xaa
1               5

(2) INFORMATION FOR SEQ ID NO: 20:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 20:

Xaa Thr Xaa Xaa Xaa Xaa
1               5

(2) INFORMATION FOR SEQ ID NO: 21:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 21:

Xaa Ser Xaa Xaa Xaa Xaa
1               5

(2) INFORMATION FOR SEQ ID NO: 22:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 22:

Xaa Thr Xaa Xaa Xaa Xaa
1               5
```

(2) INFORMATION FOR SEQ ID NO: 23:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 23:

Xaa Thr Xaa Xaa Xaa Xaa
1               5

(2) INFORMATION FOR SEQ ID NO: 24:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 24:

Xaa Ser Xaa Xaa Xaa Xaa
1               5

(2) INFORMATION FOR SEQ ID NO: 25:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 25:

Xaa Thr Xaa Xaa Xaa Xaa
1               5

(2) INFORMATION FOR SEQ ID NO: 26:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 26:

Xaa Thr Xaa Xaa Xaa Xaa
1               5

(2) INFORMATION FOR SEQ ID NO: 27:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 27:

```
Xaa Thr Xaa Xaa Xaa Xaa
 1               5
```

(2) INFORMATION FOR SEQ ID NO: 28:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 28:

```
Xaa Ser Xaa Xaa Xaa Xaa
 1               5
```

(2) INFORMATION FOR SEQ ID NO: 29:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 29:

```
Xaa Thr Xaa Xaa Xaa Xaa
 1               5
```